(12) United States Patent
Berg et al.

(10) Patent No.: US 8,008,077 B2
(45) Date of Patent: *Aug. 30, 2011

(54) PHOTOCHEMICAL INTERNALIZATION FOR DELIVERY OF MOLECULES INTO THE CYTOSOL

(75) Inventors: Kristian Berg, Heggedal (NO); Lina Prasmickaite, Olso (NO); Anders Hogset, Olso (NO); Pal Kristian Selbo, Olso (NO)

(73) Assignee: PCI Biotech AS (NO)

( * ) Notice: Subject to any disclaimer, the term of this patent is extended or adjusted under 35 U.S.C. 154(b) by 0 days.

This patent is subject to a terminal disclaimer.

(21) Appl. No.: 11/746,394

(22) Filed: May 9, 2007

(65) Prior Publication Data

US 2007/0274953 A1 Nov. 29, 2007

Related U.S. Application Data

(63) Continuation of application No. 10/433,136, filed as application No. PCT/GB01/52999 on Nov. 29, 2001, now Pat. No. 7,223,600.

(30) Foreign Application Priority Data

| Nov. 29, 2000 | (GB) | 0029134.4 |
|---|---|---|
| Dec. 1, 2000 | (GB) | 0029404.1 |
| Jun. 15, 2001 | (GB) | 0114695.0 |

(51) Int. Cl.
*C12N 15/00* (2006.01)
*C12N 15/87* (2006.01)
*A61K 48/00* (2006.01)

(52) U.S. Cl. ........... 435/455; 435/460; 435/173.5; 514/44

(58) Field of Classification Search .......... None
See application file for complete search history.

(56) References Cited

U.S. PATENT DOCUMENTS

| 5,264,618 A * | 11/1993 | Felgner et al. ........... 560/224 |
|---|---|---|
| 5,876,989 A | 3/1999 | Berg et al. |
| 6,153,639 A | 11/2000 | Sternberg et al. |
| 6,680,301 B2 | 1/2004 | Berg et al. |
| 7,223,600 B2 * | 5/2007 | Berg et al. ........... 435/455 |

FOREIGN PATENT DOCUMENTS

| GB | 2209468 A | 5/1989 |
|---|---|---|
| NO | 176786 B | 5/1985 |
| NO | 173319 B1 | 4/1986 |
| NO | 891491 | 11/1989 |
| NO | 176947 B | 5/1990 |
| NO | 176645 B | 6/1990 |
| NO | 900731 | 6/1990 |
| NO | 300499 B1 | 10/1992 |
| NO | 301981 B1 | 12/1993 |
| NO | 180742 | 4/1994 |
| WO | 9314142 A1 | 7/1993 |
| WO | 9507077 A1 | 3/1995 |
| WO | 9607432 A1 | 3/1996 |
| WO | 9628412 A1 | 9/1996 |
| WO | 9830242 A2 | 7/1998 |
| WO | 0053722 A2 | 9/2000 |
| WO | 0054802 A2 | 9/2000 |
| WO | 0209690 A2 | 2/2002 |

OTHER PUBLICATIONS

Miller et al. (FASEB J. 9: 190-199, 1995).*
Deonarain (Exp. Opin. Ther. Patents 8(1):53-69, 1998).*
Verma et al (Nature 389: 239-242, 1997).*
Crystal (Science 270: 404-410, 1995).*
Read et al (Adv. Gen. 53:19-46, 2005).*
Korbelik et al (Cancer Res. 59: 1941-1946, 1999).*
Ma et al (Rad. Res. 134: 22-28, 1993).*
Fujiwara et al (Cancer Res. 42: 1487-1491, 1982).*
Noguchi et al (Bioconjugate Chem. 3:132-137, 1992.*
Moan et al (Proc. SPIE 2625:187-193, 1996).*
Forssen et al (Proc. Am. Assoc. Cancer Res. Annual meeting) 34(0), 365, 1993).*
Pass (J. Nat. Canc. Inst. 85(6): 443-456, 1993).*
Governatore et al (Br. J. Canc. 82(1): 56-64, 2000).*
Andreansky et al (Gene Therapy 5: 121-130, 1998).*
Anderson (Nature 392:25-30, 1998).*
Romano et al (Stem Cells 18: 19-39, 2000).*
Somia and Verma (Nature Reviews Genetics 1: 91-99, 2000).*
Rosenberg et al (Science 287 :1751, 2000).*
Yokota et al (Int. J. Cancer 44(6): 1095-9, 1989).*
Fretz et al (Biochim. Biophys. Acta 1665: 48-56, 2004).*
Proffitt et al (J. Nucl. Med. 24: 45-51, 1983).*
Kitamura (Cancer Res. 51: 4310-4315, 1991).*
Prasmickaite, L. et al. "Role of endosomes in gene transfection mediated by photochemical internalisation (PCI)," The Journal of Gene Medicine (2000) 2(6): 477-488.
Rosenkranz, A. A. et al. "Targeted intracellular delivery of photosensitizers to enhance photodynamic efficiency," Immunology and Cell Biology (2000) 78(4): 452-464.
Berg, K. et al. "Lysosomes and Microtubes as Targets for Photochemotherapy of Cancer," Photochemistry and Photobiology (1997) 65: 403-409.
Berg, K. et al. "Verapamil enhances the uptake and the photocytotoxic effect of PII, but not that of terra (4-sulfonatophenyl) porphine," Biochimica et Biophysica Acta (1998) 1370: 317-324.
Berg, K. et al. "Photochemical Internalization: A Novel Technology for Delivery of Macromolecules into Cytosol," Cancer Research (1999) 59: 1180-1183.
Berg, K. et al. "Lysosomes as Photochemical Targets," Int. J. Cancer (1994) 59: 814-822.

(Continued)

*Primary Examiner* — Richard Schnizer
(74) *Attorney, Agent, or Firm* — Cantor Colburn LLP

(57) ABSTRACT

The present invention provides a method for introducing a molecule into the cytosol of a cell in which the cell is contacted with a photosensitising agent, the cell is irradiated with light of a wavelength effective to activate the photosensitising agent and, substantially at the same time or after the irradiation, the cell is contacted with the molecule to be introduced, particularly for use in cancer treatment, gene therapy and vaccination.

24 Claims, 17 Drawing Sheets

OTHER PUBLICATIONS

Berg, K. et al. "Photochemical Internalisation: A novel technology for improving macromolecule-based therapy," Photodynamic News (2001) 4: 2-5.

Canti, G. et al. "Antitumor immunity induced induced by photodynamic therapy with aluminum disulfonated phthalocyanines and laser light," Anti-Cancer Drugs (1994) 5: 443-447.

De Vree, W. J. A. et al. "Evidence for an Important Role of Neutrophilis in the Efficacy of Photodynamic Therapy in Vivo," Cancer Research (1996) 56: 2908-2911.

Dougherty, T. G. et al. "Photodynamic Therapy," Journal of the National Cancer Institute (1998) 90(12): 889-905.

Folini, M. et al. "Photochemical Internalization of a Peptide Nucleic Acid Targeting the Catalytic Subunit of Human Telomerase," Cancer Research (2003) 63: 3490-3494.

Hogset, A. et al. "Photochemical Transfection: A New Technology for Light-Induced, Site-Directed Gene Delivery," Human Gene Therapy (2000) 11: 869-880.

Korbelik, M. et al. "Photodynamic Therapy-mediated Immune Response against Subcutaneous Mouse Tumors," Cancer Research (1999) 59: 1941-1946.

Lapes, M. et al. "Photodynamic therapy of cutaneous metastases of breast cancer after local application of meso-tetra-(para-sulphophenyl)-Porphin," Journal of Photochemistry and Photobiology B (1996) 36: 205-207.

Lynch, D. H. "Systemic Immunosuppresion induced by Photodynamic Therapy (PDT) is Adoptively Transferred by Macrophages," Photochemistry and Photobiology (1989) 49: 453-458.

Moan, J. et al. "The Photodegradation of Porphyrins in Cells can to used to Estimate the Lifetime of Singlet Oxygen," Photochemistry and Photobiology (1991) 53: 549-553.

Moan, J. et al. "Sulfonated aluminium Phthalocyanines as Sensitizers for Photochemotheapy Effects of Small Light Doses of Localization, Dye Fluorescence and Photosensitivity in V79 Cells," Int. J. Cancer (1994) 58: 865-870.

Normand, N. et al. "Particle Formation by a Conserved Domain of the Herpe Simplex Virus Protein VP22 Facilitating Protein and Nucleic Acid Delivery," The Journal of Biological Chemistry (2001) 276: 15042-15050.

Prasmickaite, L. et al. "Evaluation of Different Photosensitizers for Use in Photochemical Gene Transfection," Photochemistry and Photobiology (2001) 73(4): 388-395.

Selbo, P. K. et al. "Release of gelonin from endosomes and lysosomes to cytosol by photochemical internalization," Biochimica et Biophysica Acta (2000) 1475: 307-313.

Selbo, P. K. et al. "Photochemical Internalisation Increase the Cytotoxic Effect if the Immunotoxin MOC31-Gelonin," Int. J. Cancer (2000) 87: 853-859.

Selbo, P. K. et al. "5-Aminolevulinic Acid-Based Photochemical Internalization of the Immunotoxin MOC31-gelonin Generates Synergistic Cytotoxic Effects in Vitro," Photochemistry and Photobiology (2001) 74(2): 303-310.

Selbo, P. K. et al. "In Vivo Documentation of Photochemical Internalization, a Novel Approach to Site Specific Cancer Therapy," Int. J. Cancer (2001) 92: 761-766.

Thilo, L. et al. "Maturation of early endosomes and vesicular traffic to lysosomes in relation to membrane recycling," Journal of Cell Science (1995) 108: 1791-1803.

Verma et al (Nature 389: 239-242, 1997).

Anderson (Nature 392: 25-30, 1998).

Romano et al (Stem Cells 18: 19-39, 2000).

Somia and Verma (Nature Reviews Genetics 1: 91-99, 2000).

Ma et al (Rad. Res. 134: 22-28, 1993).

Fujiwara et al (Cancer Res. 42: 1487-1491, 1982).

Noguchi et al (Bioconjugate Chem. 3: 132-137, 1992).

Moan et al (Proc. SPIE 2625: 187-193, 1996).

Forssen et al (Proc. Am. Assoc. Cancer Res. Annual meeting) 34(0), 365, 1993.

Dermer (Biotechnology 12: 320, 1994).

* cited by examiner

A

B

C

PHOTOCHEMICAL INTERNALIZATION FOR DELIVERY OF MOLECULES INTO THE CYTOSOL

CROSS-REFERENCE TO RELATED APPLICATION

This application is a continuation of, U.S. patent application Ser. No. 10/433,136, filed on Nov. 10, 2003, now issued as U.S. Pat. No. 7,223,600, which was a §371 National Stage application of PCT/GB01/052999 filed on Nov. 29, 2001, which claims priority to Great Britain Application No. 0029134.4, filed Nov. 29, 2000, Great Britain Application No. 0029404.1, filed Dec. 1, 2000, and to Great Britain Application No. 0114695.0, filed on Jun. 15, 2001, the disclosures of which are herein incorporated by reference in its entirety.

METHOD

The present invention relates to an improved method for introducing molecules into the cytosol of cells using a photosensitising agent and irradiation of the cells with light of a wavelength effective to activate the photosensitising agent.

The majority of molecules do not readily penetrate cell membranes. Methods for introducing molecules into the cytosol of living cells are useful tools for manipulating and studying biological processes. Among the most commonly used methods today are microinjection, red blood cell ghost-mediated fusion and liposome fusion, osmotic lysis of pinosomes, scrape loading, electroporation, calcium phosphate and virus-mediated transfection. These techniques are useful for investigating cells in culture, although in many cases they may be impractical, time consuming, inefficient or they may induce significant cell death. Thus such techniques are not optimal for use in biological or medical research, or in therapies where it is required that cells should remain viable and/or functional.

It is well known that porphyrins and many other photosensitizing compounds may induce cytotoxic effects on cells and tissues. These effects are based upon the fact that upon exposure to light the photosensitizing compound may become toxic or may release toxic substances such as singlet oxygen or other oxidising radicals which are damaging to cellular material or biomolecules, including the membranes of cells and cell structures, and such cellular or membrane damage may eventually kill the cells. These effects have been utilised in the treatment of various abnormalities or disorders, including especially neoplastic diseases. The treatment is named photodynamic therapy (PDT) and involves the administration of photosensitizing (photochemotherapeutic) agents to the affected area of the body, followed by exposure to activating light in order to activate the photosensitizing agents and convert them into cytotoxic form, whereby the affected cells are killed or their proliferative potential diminished. Photosensitizing agents are known which will localise preferentially or selectively to the desired target site e.g. to a tumour or other lesion.

A range of photosensitizing agents are known, including notably the psoralens, the porphyrins, the chlorins and the phthalocyanins. Such drugs become toxic when exposed to light.

Photosensitizing drugs may exert their effects by a variety of mechanisms, directly or indirectly. Thus for example, certain photosensitisers become directly toxic when activated by light, whereas others act to generate toxic species, e.g. oxidising agents such as singlet oxygen or other oxygen-derived free radicals, which are extremely destructive to cellular material and biomolecules such as lipids, proteins and nucleic acids.

Porphyrin photosensitisers act indirectly by generation of toxic oxygen species, and are regarded as particularly favourable candidates for PDT. Porphyrins are naturally occurring precursors in the synthesis of heme. In particular, heme is produced when iron ($Fe^{3+}$) is incorporated in protoporphyrin IX (PpIX) by the action of the enzyme ferrochelatase. PPIX is an extremely potent photosensitizer, whereas heme has no photosensitizing effect. A variety of porphyrin-based or porphyrin-related photosensitisers are known in the art and described in the literature.

The cytotoxic effect of most sensitizers used in PDT is mediated mainly through the formation of singlet oxygen formed upon exposure of the photosensitizers to light. This reactive intermediate has a very short lifetime in cells (<0.04 μs). Thus, the primary cytotoxic effect of PDT is executed during light exposure and very close to the sites of formation of $^1O_2$. $^1O_2$ reacts with and oxidizes proteins (histidine, tryptophan, methionine, cysteine, tyrosine), DNA (guanine), unsaturated fatty acids and cholesterol. One of the advantages of PDT is that tissues unexposed to light may be left unaffected ie. that a selective PDT effect may be obtained. There is extensive documentation regarding use of PDT to destroy unwanted cell populations, for example neoplastic cells. The patent literature describes a number of photodynamic compounds, alone or conjugated with targeting agents, e.g. immunoglobulins directed to neoplastic cell receptor determinants, making the complex more cell specific. Certain photochemical compounds, such as hematoporphyrin derivatives, have furthermore an inherent ability to localise in malignant cells. Such methods and compounds, are described in the Norwegian patent No. 173319 and in Norwegian patent applications Nos. 90 0731, 176 645, 176 947, 180 742, 176 786, 301 981, 30 0499 and 89 1491.

In WO93/14142 a drug delivery system is described which comprises an anti-cancer agent and a photoactivatable agent (ie. a photosensitizer) attached to copolymeric carriers. Upon administration this complex enters the cell interior by pinocytosis or phagocytosis and locates inside the endosomes and lysosomes. In the lysosomes, the bond between the antineoplastic agent and the polymer is hydrolysed and the former can diffuse passively through the lysosome membrane into the cytosol. The utility of this method is thus limited to small molecular compounds which are able to diffuse across the lysosome membranes. After allowing a time lag for diffusion, a light source of appropriate wavelength and energy is applied to activate the photo-activatable compound. The combined effect of the anti-cancer agent and photoactivatable agent destroy the cell. Such PDT methods as described above are thus directed to the destruction of cell structures leading to cell death.

WO 96/07432 and WO 00/54802 on the other hand, are concerned with methods which use the photodynamic effect as a mechanism for introducing otherwise membrane-impermeable molecules into the cytosol of a cell in a manner which does not necessarily result in widespread cell destruction or cell death. In this method, the molecule to be internalised and a photosensitising compound are applied simultaneously or in sequence to the cells, upon which the photosensitizing compound and the molecule are endocytosed or in other ways translocated into endosomes, lysosomes or other intracellular membrane restricted compartments.

The molecule to be translocated into intracellular compartments of the cells and the photosensitising compound are applied to the cells together or sequentially and are taken up by the cell together into the same intracellular compartments (i.e. are co-translocated). The molecule to be internalised within the cell is then released by exposure of the cells to light of suitable wavelengths to activate the photosensitising compound which in turn leads to the disruption of the intracellular compartment membranes and the subsequent release of the molecule, which is located in the same compartment as the photosentizing agent, into the cytosol. This method was termed "photochemical internalisation" or PCI. Thus, in these methods the final step of exposing the cells to light results in the molecule in question being released from the same intracellular compartment as the photosensitizing agent and becoming present in the cytosol.

It was believed that in order for this method to be effective it was essential that both the photosensitising compound and the molecule to be released into the cytosol were present in the same intracellular compartments when irradiation was performed.

It has now surprisingly been found that molecules can be introduced into the cytosol of cells by similar PCI methods but where the exposure of the cells to light is not necessarily the final step and the methods are not dependent on the molecule and the photosensitizing agent being located in the same intracellular compartments at the time of light exposure. In such methods the photosensitising agent may be contacted with the cells and activated by irradiation before the molecule to be internalised and thus delivered to the cytosol is brought into contact with the cells. Thus, despite the fact that the molecule to be internalised and the photosensitising agent are not necessarily localised in the same intracellular compartments at the time of light exposure, the molecule still enters the cell and is delivered to the cytosol. These results are extremely surprising and such methods display significant advantages over the methods where light irradiation is the final step.

At its most general therefore, the present invention provides a method for introducing a molecule into the cytosol of a cell, said method comprising contacting said cell with a photosensitising agent, contacting said cell with the molecule to be introduced and irradiating said cell with light of a wavelength effective to activate the photosensitising agent, wherein said irradiation is performed prior to the cellular uptake of said molecule into an intracellular compartment containing said photosensitising agent, preferably prior to cellular uptake of said molecule into any intracellular compartment.

Thus in one alternative, said irradiation can be performed after the cellular uptake of the molecule into an intracellular compartment, providing said molecule to be internalised and the photosensitising agent are not localised in the same intracellular compartments at the time of light exposure. In a preferred embodiment however irradiation is performed prior to cellular uptake of the molecule to be internalised.

"Internalisation" as used herein, refers to the cytosolic delivery of molecules. In the present case "internalisation" thus includes the step of release of molecules from intracellular/membrane bound compartments into the cytosol of the cells.

As used herein, "cellular uptake" or "translocation" refers to one of the steps of internalisation in which molecules external to the cell membrane are taken into the cell such that they are found interior to the outerlying cell membrane, e.g. by endocytosis or other appropriate uptake mechanisms, for example into or associated with an intracellular membrane-restricted compartments, for example the endoplasmic reticulum, Golgi body, lysosomes, endosomes etc.

In particular, viewed from a preferred aspect the present invention provides a method for introducing a molecule into the cytosol of a cell, said method comprising contacting said cell with a photosensitising agent, irradiating said cell with light of a wavelength effective to activate the photosensitising agent and, substantially at the same time or at a time after the irradiation, contacting said cell with the molecule to be introduced.

Preferably the cells are contacted with the molecules to be introduced or internalised (referred to hereinafter as the transfer molecules) at a time point after irradiation has taken place, or in other words, photochemical treatment of the cells, by contacting them with a photosensitising agent and then irradiation, is effected before the molecules are added to the cells. In this embodiment the molecules to be introduced into the cytosol can be brought into contact with the cells which have been subjected to photochemical treatment at any time point after the treatment has occurred providing the transfer molecules are still able to be taken up into the cells. The time window in which the molecules may be brought into contact with the cells and still be taken up may depend on a variety of factors such as for example the cell type, the particular molecule in question, the particular photosensitising agent used, and the duration of the light treatment. This time window can if necessary be determined for a particular set of conditions. However, preferably the molecule to be transferred to the cytosol is exposed to the cells relatively soon after photochemical treatment, for example within 24 hours after photochemical treatment and more preferably within the first 10 hours after photochemical treatment e.g. within the first 5 hours or more preferably the first hour. For example in vitro or ex vivo the transfer molecule may be administered for a certain time period, e.g. 30 minutes to 24 hours, preferably 1 to 2 hours, commencing administration immediately after or shortly after irradiation, e.g. if the end of irradiation is considered as the start point, the transfer molecule may be applied at 0 minutes to 24 hours, e.g. 0 to 4 hours.

It has been observed that even if the transfer molecule is contacted with the cell a considerable time after irradiation, internalization into the cell is still possible. Thus, for example, the transfer molecule may be applied more than an hour after irradiation, e.g. more than 2, 4, 8, 10 or even 12 hours after irradiation.

Thus, in a preferred embodiment said cell is contacted with said transfer molecule 0 to 4 hours after irradiation for a period of 1 to 2 or 3 hours or longer, e.g. at least 0.5 to 3 hours. The time at which the transfer molecule is administered will vary depending on whether the methods are being carried out in vitro or in vivo. For in vitro methods the transfer molecules can generally be brought into contact with all the target cells simultaneously, e.g. if the cells are growing in an in vitro culture and thus it is relatively easy to bring the molecules in contact with the cells at an appropriate time point. In vivo however, the step of contacting the target cells with the transfer molecules is clearly more complicated and will depend on the mode of administration and the location of the target cells.

For example, where the transfer molecule can be administered directly to the target cells, e.g. by local injection, then the transfer molecule will come into contact with the target cells (or at least a proportion of them) relatively quickly, e.g. in a matter of minutes or hours after administration. If on the other hand the transfer molecules are administered by intravenous injection for a distant target then these molecules may take a lot longer to come into contact with the target cells. For example they may take 24 to 96 hours after administration to reach the target cells. This "journey time" will have to be taken into account in deciding the appropriate time for which to administer the transfer molecules relative to the administration of the photosensitizing agent and the time of irradiation.

In an alternative embodiment of the invention rather than the transfer molecule being brought into contact with the cells after irradiation has taken place it can be brought into contact with the cells substantially at the same time as the irradiation. "Substantially at the same time" as used herein includes exactly at the same time i.e. simultaneously, but also includes the addition of the molecule to the cells shortly before irradiation, for example up to one or two hours before irradiation, providing that the cellular uptake of the transfer molecule has not occurred at the time of irradiation and may still occur, albeit after irradiation or providing that if cellular uptake of the transfer molecule has occurred then the transfer molecule and the photosensitizing agent are not localised to the same intracellular compartments at the time of light exposure.

As mentioned above, the precise timing of the addition of the transfer molecule and photosensitizing agent and timing of irradiation to achieve the above described effects need to take into account various factors including the cells to be treated, agents and molecules in use and the environment of the cells, particularly with regard to whether an in vitro or in vivo system is in issue. Taking these considerations into account appropriate timings may readily be determined.

As a general principle appropriate conditions are determined such that the irradiation step should take place either prior to the cellular uptake of the transfer molecule (assuming that the photosensitizing agent itself has been take up into intracellular compartments) or after the cellular uptake of the transfer molecule provided that the transfer molecule and the photosensitizing agent are not located in the same intracellular compartments at the time of light exposure. In this latter scenario, clearly the transfer molecule will come into contact with the cells at a time point before irradiation takes place. This provides one of the preferred embodiments of the present invention.

Previously disclosed methods of photochemical internalisation wherein the transfer molecule and the photosensitising agent were added to the cells prior to irradiation depended on the molecules in question being located in the same intracellular compartments prior to light exposure so that lysis of these compartments by the light activation of the photosensitising agent resulted in the release of both the molecule and the photosensitising agent into the cytosol. A schematic drawing showing this is shown in FIG. 7.

In the present methods clearly the photosensitising agent and the transfer molecule to be introduced into the cytosol are not in the same intracellular compartments at the time of light exposure since the transfer molecule is only added to the cells shortly before or after the cells are exposed to light.

The mechanism of action of the present methods is as yet unknown and indeed the fact that this method works at all is surprising. Whilst not wishing to be bound by theory, the reason for these surprising findings may be that fusion of photochemically damaged vesicles with newly formed endocytotic vesicles takes place which is then followed by the release of newly endocytosed molecules into the cytosol. A schematic diagram illustrating this is shown in FIG. 7. Alternatively, photochemical damage to lysosomal enzymes or vesicles containing lysosomal enzymes, such as late endosomes, may reduce the rate of intracellular degradation of the molecules to be internalized. This may be due to reduced transport to vesicles containing lysosomal enzymes or transport to endocytic vesicles containing lower hydrolytic activity. In this way these molecules will have more time to escape the endocytic compartmentalization than when the lysosomal degradation pathway is active. A further alternative explanation could be that the photochemical treatment of the cells leads to minor damage to the plasma membrane of the cells leading to increased penetration of macromolecules through the cell membrane. However experiments carried out (see Example 7) suggest that this is probably not the reason.

The present invention thus relates to methods for transporting or transfecting any molecules into the cytosol of living cells either in vitro (i.e. in culture) or in vivo, after which the molecules shall be available in the cytosol.

Such methods can be used not only to transfer molecules (or parts or fragments thereof) into the interior of a cell but also, in certain circumstances, to present or express them on the cell surface. Thus, following transport and release of a transfer molecule into the cell cytosol according to the methods of the present invention, if the cell(s) in question are specialised cells, such as for example antigen presenting cells, the molecule or fragment, may be transported to the surface of the cell where it may be presented on the outside of the cell ie. on the cell surface. Such methods have particular utility in the field of vaccination, where vaccine components ie. antigens or immunogens, may be introduced into a cell for presentation on the surface of that cell, in order to induce, facilitate or augment an immune response. Further details as to the utility of being able to express molecules on the cell surface are described in WO 00/54802.

The transfer molecules which can be introduced into the cytosol of cells using the methods of the present invention include molecules which do not readily penetrate cell membranes. Additionally, the present invention can increase the cytosol delivery and activity of molecules which are only partly able to penetrate the membrane of the cell or the membranes of intracellular vesicles. Transfer molecules may be organic compounds, proteins or fragments of proteins such as for example peptides, antibodies or antigens or fragments thereof. Another class of transfer molecules for use according to the invention are cytotoxic drugs such as protein toxins or cytotoxic organic compounds, e.g. bleomycin. Still another class of appropriate transfer molecules are nucleic acids.

Nucleic acids may be used in the form of genes encoding for example therapeutic proteins, antisense RNA molecules, ribozymes, RNA aptamers or triplex forming oligonucleotides. Alternatively the nucleic acids may be employed in the form of non-encoding molecules such as for example synthetic DNA or RNA antisense molecules, ribozymes, aptamers, triplex forming oligonucleotides, peptide nucleic acids (PNAs), transcription factor "decoy" DNA or chimeric oligonucleotides for repair of specific mutations in the patient. Where appropriate the nucleic acid molecules may be in the form of whole genes or nucleic acid fragments optionally incorporated into a vector molecule or entity e.g. a plasmid vector or a viral particle or bacteriophage. The latter form has particular applicability when the transfer molecule is to be used in methods of gene therapy.

The photosensitizing agent to be used according to the present invention is conveniently any such agent which localises to intracellular compartments, particularly endosomes or lysosomes. A range of such photosensitising agents are known in the art and are described in the literature, including in WO96/07432. Mention may be made in this respect of di- and tetrasulfonated aluminium phthalocyanine (e.g. $AlPcS_{2a}$), sulfonated tetraphenylporphines ($TPPS_n$), nile blue, chlorin $e_6$ derivatives, uroporphyrin I, phylloerythrin, hematoporphyrin and methylene blue which have been shown to locate in endosomes and lysosomes of cells in culture. This is in most cases due to endocytic uptake of the photosensitizer. Thus, the photosensitizing agent is preferably an agent which is taken up into the internal compartments of lysosomes or endosomes. However, other photosensitizing agents which locate to other intracellular compartments for example the endoplasmic reticulum or the Golgi apparatus may also be used. It is also conceivable that mechanisms may be at work where the effects of the photochemical treatment are on other components of the cell (i.e. components other than membrane-restricted compartments). Thus, for example one possibility may be that the photochemical treatment destroys molecules important for intracellular transport or vesicle fusion. Such molecules may not necessarily be located in membrane-restricted compartments, but the photochemical damage of such molecules may nevertheless lead to photochemical internalisation of the transfer molecules, e.g. by a mechanism where photochemical effects on such molecules lead to reduced transport of the molecule to be internalized (i.e. the transfer molecule) to degradative vesicles such as lysosomes, so that the molecule to be internalized can escape to the cytosol before being degraded. Examples of such molecules not necessarily located in membrane restricted compartments are several molecules of the microtubular transport system like dynein and components of dynactin; and for example rab5, rab7, N-ethylmaleimde sensitive factor (NSF), soluble NSF attachment protein (SNAP) and so on.

Classes of suitable photosensitising agents which may be mentioned thus include porphyrins, phthalocyanines, purpurins, chlorins, benzoporphyrins naphthalocyanines, cationic dyes, tetracyclines and lysomotropic weak bases or derivatives thereof (Berg et al., J. Photochemistry and Photobiology, 1997, 65, 403-409). Other suitable photosensitising agents include texaphyrins, pheophorbides, porphycenes, bacteriochlorins, ketochlorins, hematoporphyrin derivatives, and derivatives thereof, endogenous photosensitizers induced by 5-aminolevulinic acid and derivatives thereof, dimers or other conjugates between photosensitizers.

Preferably the photosensitizer is in free form, ie. not conjugated to any other macromolecule. However the photosensitizer may alternatively be associated with, attached to, or conjugated to, a carrier or other molecule as described hereinafter, e.g. attached to a targeting antibody or coupled to a carrier such as polylysine.

Preferred photosensitising agents include $TPPS_4$, $TPPS_{2a}$, $AlPcS_{2a}$ and other amphiphilic photosensitizers. In a preferred aspect, the present invention provides methods in which the photosensitizing agents which may be used are compounds being 5-aminolevulinic acid or esters of 5-aminolevulinic acid or pharmaceutically acceptable salts thereof.

In such esters the 5-amino group may be substituted or unsubstituted, the latter case being the ALA esters.

More particularly, the ALA esters for use according to the invention are esters of 5-aminolevulinic acids with optionally substituted alkanols, ie. alkyl esters or substituted alkyl esters.

Conveniently, ALA esters which may be used are compounds of formula I,

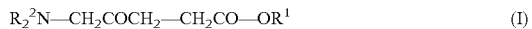

$$R_2^2N\text{---}CH_2COCH_2\text{---}CH_2CO\text{---}OR^1 \quad (I)$$

(wherein $R^1$ may represent alkyl optionally substituted by hydroxy, alkoxy, acyloxy, alkoxycarbonyloxy, amino, aryl, oxo or fluoro groups and optionally interrupted by oxygen, nitrogen, sulphur or phosphorus atoms; and $R^2$, each of which may be the same or different, represents a hydrogen atom or a group $R^1$) and salts thereof.

The substituted alkyl $R^1$ groups may be mono or poly-substituted. Thus suitable $R^1$ groups include for example unsubstituted alkyl, alkoxyalkyl, hydroxyalkoxyalkyl, poly-hydroxyalkyl, hydroxy poly alkyleneoxyalkyl and the like. The term "acyl" as used herein includes both carboxylate and carbonate groups, thus, acyloxy substituted alkyl groups include for example alkylcarbonyloxy alkyl. In such groups any alkylene moieties preferably have carbon atom contents defined for alkyl groups below. Preferred aryl groups include phenyl and monocyclic 5-7 membered heteroaromatics, especially phenyl and such groups may themselves optionally be substituted.

Representative substituted alkyl groups $R^1$ include alkoxymethyl, alkoxyethyl and alkoxypropyl groups or acyloxymethyl, acyloxyethyl and acyloxypropyl groups eg. pivaloyloxymethyl.

Preferred ALA esters for use as photosensitizing agents according to the invention, include those wherein $R^1$ represents an unsubstituted alkyl group and/or each $R^2$ represents a hydrogen atom.

As used herein, the term "alkyl" includes any long or short chain, straight-chained or branched aliphatic saturated or unsaturated hydrocarbon group. The unsaturated alkyl groups may be mono- or polyunsaturated and include both alkenyl and alkynyl groups. Such groups may contain up to 40 carbon atoms. However, alkyl groups containing up to 10 eg. 8, more preferably up to 6, and especially preferably up to 4 carbon atoms are preferred.

Particular mention may be made of ALA-methylester, ALA-ethylester, ALA-propylester, ALA-hexylester, ALA-heptylester and ALA-octylester and salts thereof, which represent preferred photosensitizing agents for use according to the invention.

Necessarily, the photosensitising agent is contacted with a cell prior to irradiation. However, unlike the transfer molecule, this agent should be administered sufficiently prior to irradiation such that on irradiation said agent has been taken up into an intracellular compartment. Thus conveniently said agent is applied 1 to 72 hours prior to irradiation, e.g. 4 to 48 e.g. 4 to 24 hours prior to irradiation. Again, as discussed above in connection with the step of bringing the transfer molecule into contact with the cells, the timing of administration of the photosensitizing agent to achieve contact with the target cell in relation to the time point of irradiation will depend on the time it will take for a photosensitizing agent to reach the target cells and be taken up by them. This time may vary depending on whether the methods are being carried out in vitro or in vivo and on whether the administration is direct to the target tissue or is at a distal site. In all cases, it is important that the photosensitizing agent has been taken up by the target cells before irradiation takes place. Said agent may be maintained in contact with said cells immediately up to irradiation, e.g. for 1 or 4 to 72 hours, preferably 4 to 24 hours, e.g. 12 to 20 hours, or may be removed from contact immediately prior to irradiation, e.g. for more than 5 minutes, e.g. for 10 minutes to 8 hours, e.g. 1 hour to 4 hours in agent-free medium.

Optionally, one or other or both of the photosensitising agent and the transfer molecule to be introduced into cells may be attached to or associated with or conjugated to one or more carrier molecules, targetting molecules or vectors which can act to facilitate or increase the uptake of the photosensitising agent or the transfer molecule or can act to target or deliver these entities to a particular cell type, tissue or intracellular compartment. Examples of carrier systems include polylysine or other polycations, dextran sulphate, different cationic lipids, liposomes, reconstituted LDL-particles, sterically stabilised liposomes or adenovirus particles.

These carrier systems can generally improve the pharmacokinetics and increase the cellular uptake of the transfer molecule and/or the photosensitizing agent and may also direct the transfer molecule and/or the photosensitizing agent to intracellular compartments that are especially beneficial for obtaining photochemical internalisation, but they do not generally have the ability to target the transfer molecule and/or the photosensitizing agent to specific cells (e.g. cancer cells) or tissues. However, to achieve such specific or selective targeting the carrier molecules, the transfer molecule and/or the photosensitizer may be associated or conjugated to specific targetting molecules that will promote the specific cellular uptake of the transfer molecule into desired cells or issues. Such targetting molecules may also direct the transfer molecule to intracellular compartments that are especially beneficial for obtaining photochemical internalisation.

Many different targeting molecules can be employed, e.g. as described in Curiel, D. T. (1999), Ann. New York Acad. Sci. 886, 158-171; Bilbao, G. et al. (1998), in Gene Therapy of Cancer (Walden et al., eds., Plenum Press, New York), Peng K. W. and Russell S. J. (1999), Curr. Opin. Biotechnol. 10, 454-457, Wickham T. J. (2000), Gene Ther. 7, 110-114.

The carrier molecule and/or the targetting molecule may be associated, bound or conjugated to the transfer molecule, to the photosensitizing agent or both, and the same or different carrier or targeting molecules may be used. If for example adenovirus particles are used as carriers then the transfer molecules may be incorporated within the adenovirus particles. For example if the transfer molecule in question is a DNA molecule encoding a protein or an RNA molecule, then the DNA is incorporated into the virus vector and after photochemical internalisation the DNA molecule will be present at the correct intracellular location so that expression of the encoded molecule can occur.

Expression of such molecules can be controlled by designing the vector by methods well known and documented in the art. For example, regulatory elements such as for example tissue specific or regulatable promoters can be used to obtain tissue or disease specific or regulatable expression. For example the tissue specific promoter melanoma specific tyrosinase promoter may be used. Regulatable promoters such as tetracylin-regulated promoters are well known. More examples of specific or regulated promoters that can be employed in the present invention can be found in Hart, I. R., 1996, *Semin. Oncol.* 23, 154-158; Hallahan, D. E. et al., 1995, *Nature Med.* 1, 786-791; Luna, M. C. et al. 2000, *Cancer Res.* 60, 1637-1644; Miller, N. and Whelan, J., 1997, *Hum. Gene Ther.*; Wickham, T. J, 2000, *Gene Ther.* 7, 110-114; Nettelbeck D. M. and Muller; J. V., 2000, *Trends Genet.* 16, 174-181; Clackson, T., 2000, *Gene Ther.* 7, 120-125; Freundlieb, S, et al., 1999, J. Gene Med. 1, 4-12; Spear M. A., 1998, *Anticancer Res.* 18, 3223-31, Harvey, D. M. and Caskey C. T., 1998, *Curr. Opin. Chem. Biol.* 2, 512-518; Clary, B. M. and Lyerly, H. K., 1998, *Surg. Oncol. Clin. North Am.* 7, 565-574. Luna, M C et al. *Cancer Res.* 60, 1637-1644; and the references therein.

As mentioned above, more than one carrier and/or targeting molecule or vector may be used simultaneously.

For example vectors may be provided in a carrier, e.g. viral vectors such as adenovirus may be carried, eg. in a liposome or polycation structure.

Preferred carriers and vectors for use in the present invention, particularly for use in conjunction with the transfer molecule, include adenoviruses, polycations such as polylysine (e.g. poly-L-lysine or poly-D-lysine), polyethyleneimine or dendrimers (e.g. cationic dendrimers such as Super-Fect®); cationic lipids such as DOTAP or Lipofectin; peptides and targeted vectors such as e.g. transferrin polylysine or targeted adenovirus vectors. In a particularly preferred embodiment of the invention the carrier is adenovirus.

Such targeting molecules or carriers as described above may also be used to direct the transfer molecule to particular intracellular compartments especially beneficial for the employment of PCI, for example lysosomes or endosomes.

The intracellular membrane-restricted compartment may be any such compartment which is present in a cell.

Preferably the compartment will be a membrane vesicle, especially an endosome or a lysosome. However, the intracellular compartment may also include the Golgi apparatus or the endoplasmic reticulum.

The light irradiation step to activate the photosensitising agent may take place according to techniques and procedures well known in the art. For example, the wavelength and intensity of the light may be selected according to the photosensitising agent used. Suitable light sources are well known in the art.

The time for which the cells are exposed to light in the methods of the present invention may vary. The efficiency of the internalisation of the transfer molecule into the cytosol appears to increase with increased exposure to light. A preferred length of time for the irradiation step depends on the photosensitizer, the amount of the photosensitizer accumulated in the target cells or tissue and the overlap between the absorption spectrum of the photosensitizer and the emission spectrum of the light source. Generally, the length of time for the irradiation step is in the order of minutes to several hours, e.g. preferably up to 60 minutes e.g. from 0.5 or 1 to 30 minutes, e.g. from 0.5 to 3 minutes or from 1 to 5 minutes or from 1 to 10 minutes e.g. from 3 to 7 minutes, and preferably approximately 3 minutes, e.g. 2.5 to 3.5 minutes. Appropriate light doses can be selected by a person skilled in the art and again will depend on the photosensitizer and the amount of photosensitizer accumulated in the target cells or tissues. For example, the light doses typically used for photodynamic treatment of cancers with the photosensitizer Photofrin and the protoporphyrin precursor 5-aminolevulinic acid is in the range 50-150 J/cm$^2$ at a fluence range of less than 200 mW/cm$^2$ in order to avoid hyperthermia. The light doses are usually lower when photosensitizers with higher extinction coefficients in the red area of the visible spectrum are used. However, for treatment of non-cancerous tissues with less photosensitizer accumulated the total amount of light needed may be substantially higher than for treatment of cancers.

Determining the appropriate doses of target molecules for use in the methods of the present invention would be routine practice for a person skilled in the art. Where the transfer molecule is a protein or peptide, for in vitro applications the transfer molecules would generally be used at doses of less than 5 mg/ml (e.g 0.1-5 mg/ml) and for in vivo applications the transfer molecules would generally be used at doses of less than 5 mg/kg (e.g. 0.1-5 mg/kg). Where the transfer molecule is a nucleic acid, for in vitro applications an exemplary dose of the transfer molecules would be approximately 0.1-50 µg nucleic acid per 10$^4$ cells and for in vivo applications approximately 10$^{-6}$-1 g nucleic acid per injection in humans. Where the transfer molecule is associated with an adenovirus carrier, for in vitro applications an exemplary dose would be between 1-1×10$^5$ physical virus particles, e.g. 1×10$^3$-10×10$^5$ particles per cell and for in vivo applications the molecule to be introduced in association with the adenoviral carrier may be present at a concentration of 1×10$^{-9}$ to 50% such as 3×10$^{-6}$ to 50%, e.g. 0.003 to 30%, e.g. 0.2 to 10% (w/w) of virus particles in the final composition for use in vivo in which w/w refers to the weight of the viral carrier in addition to the molecule to be introduced relative to the weight of the final composition. If used in 1 ml injections, this would correspond to a dose of approximately $10^5$ to $10^{15}$ physical viral particles.

The methods of the invention will inevitably give rise to some cell killing by virtue of the photochemical treatment i.e. through the action of the photosensitizing agent. However, this cell death will not matter and may indeed be advantageous for many of the applications (e.g. cancer treatment) and the methods of the invention may be modified such that the fraction or proportion of the surviving cells is regulated by selecting the light dose in relation to the concentration of the photosensitivity agent. Again, such techniques are known in the art. Regardless of the amount of cell death induced by the pure photochemical treatment, it is important that the light dose is regulated such that some of the individual cells wherein the PCI effect is manifested are not killed by pure photochemical treatment (although they may subsequently be killed due to the PCI effect).

In some applications it may be appropriate to retain a larger number of viable cells after PCI treatment. For example in vaccination and some gene therapy methods viable cells which allow for example antigen presentation or protein expression is important.

In such applications it is appropriate that a population or plurality of cells, substantially all of the cells, or a significant majority (e.g. at least 50%, more preferably at least 60, 70, 80 or 90% of the cells) are not killed. This of course is not always desirable especially when PCI is used to introduce cytotoxic transfer molecules and further cell killing is not disadvantageous. Cytotoxic effects may also however be achieved by using for example gene therapy in which a therapeutic gene is internalized into tumour cells by the method of the invention e.g. so that these cells will produce immunologically active substances that will induce local immunological killing of remaining cancer cells or induce a systemic immune response to the tumour cells. In such cases, clearly after PCI treatment a proportion of viable cells are required.

The advantages of the present methods and the sequence of treatment steps, especially the embodiments wherein the transfer molecule is added to the cells after the light irradiation step, as compared to the previously described methods are a) photochemical damage to the transfer molecule is diminished;

b) simplification of PCI treatment of internal lesions in combination with surgery since photochemical treatment may be performed after surgical exposure of the lesion followed by e.g. intratumoral injection or other local administration of the transfer molecule;

c) the methods are more independent of exact timing of treatment, i.e. the timing of the addition of the molecule to be taken up by the cells relative to the time point of illumination. This means that there is a greater "time window" for treatment. This is important since uptake of a therapeutic molecule can vary widely in different clinical situations and moreover, the uptake is difficult to estimate for individual lesions in a clinical situation, therefore making a greater time window extremely advantageous;

d) rapid translocation of the transfer molecule to the cytosol occurs thereby substantially decreasing the possibilities for lysosomal degradation of the transfer molecule.

These advantages are in addition to the advantages associated with PCI methods of internalisation of molecules per se, i.e. 1) there is no restriction on the size of the molecule to be internalised and delivered to the cytosol as long as the molecule can be endocytosed by the target cell; 2) the methods are not dependent on cell proliferation; 3) the methods are site specific in that only areas exposed to light are affected; 4) it is not oncogenic.

The steps of "contacting" the cells with a photosensitising agent and with the transfer molecule may be carried out in any convenient or desired way. Thus, if the contacting step is to be carried out in vitro the cells may conveniently be maintained in an aqueous medium such as for example appropriate cell culture medium and at the appropriate time point the photosensitising agent or transfer molecule can simply be added to the medium under appropriate conditions, for example at an appropriate concentration and for an appropriate length of time.

The photosensitizing agent is brought into contact with the cells at an appropriate concentration and for an appropriate length of time which can easily be determined by a skilled person using routine techniques and will depend on the particular photosensitizing agent used and the cell type. The concentration of the photosensitizing agent must be such that once taken up into the cell, e.g. into, or associated with, one or more of its intracellular compartments and activated by irradiation, one or more cell structures are disrupted e.g. one or more intracellular compartments are lysed or disrupted. For example photosensitising agents used in the Examples herein may be used at a concentration of for example 10 to 50 μg/ml. For in vitro use the range can be much broader, e.g. 0.05-500 μg/ml. For in vivo human treatments the photosensitizing agent may be used in the range 0.05-20 mg/kg body weight when administered systemically or 0.1-20% in a solvent for topical application. In smaller animals the concentration range may be different and can be adjusted accordingly.

The time of incubation of the cells with the photosensitizing agent (i.e. the "contact" time) can vary from a few minutes to several hours, e.g. even up to 48 hours or longer. The time of incubation should be such that the photosensitizing agent is taken up by the appropriate cells.

The incubation of the cells with the photosensitizing agent may optionally be followed by a period of incubation with photosensitiser free medium before the cells are exposed to light or the transfer molecule is added.

The transfer molecule can be any molecule as discussed above and is brought into contact with the cells at an appropriate concentration and for an appropriate length of time. Surprisingly it has been found that the contact may be initiated even several hours after irradiation. An appropriate concentration can be determined depending on the efficiency of uptake of the molecule in question into the cells in question and the final concentration it is desired to achieve in the cells. Thus "transfection time" or "cellular uptake time" i.e. the time for which the molecules are in contact with the cells can be a few minutes or up to a few hours, for example a transfection time of from 10 minutes until up to 24 hours, for example 30 minutes up to 10 hours or for example 30 minutes until up to 2 hours or 6 hours can be used. An increased transfection time usually results in increased uptake of the molecule in question. However, the shorter incubation times, for example 30 minutes to 1 hour, seem to result in an improved specificity of the uptake of the molecule. Thus, in selecting a transfection time for any method, an appropriate balance must be struck between obtaining a sufficient uptake of the molecule while maintaining sufficient specificity of uptake.

In vivo an appropriate method and time of incubation by which the transfer molecules and photosensitizing agents are brought into contact with the target cells will be dependent on the mode of administration and the type of transfer molecule and photosensitizing agents. For example, if the transfer molecule is injected into a tumour which is to be treated, the cells near the injection point will come into contact with and hence tend to take up the transfer molecule more rapidly than the cells located at a greater distance from the injection point, which are likely to come into contact with the transfer molecule at a later timepoint and lower concentration. In addition, a transfer molecule given by intravenous injection may take some time to arrive at the target cells and it may thus take longer post-administration e.g. several days, in order for a sufficient or optimal amount of the transfer molecule to accumulate in a target cell or tissue. The same considerations of course apply to the time of administration required for the uptake of the photosensitizing agent into cells. The time of administration required for individual cells in vivo is thus likely to vary depending on these and other parameters.

Nevertheless, although the situation in vivo is more complicated than in vitro, the underlying concept of the present invention is still the same, i.e. the time at which the molecules come into contact with the target cells must be such that before irradiation occurs an appropriate amount of the photosensitizing agent has been taken up by the target cells and either: (i) before or during irradiation the transfer molecule has either been taken up, or will be taken up after sufficient contact with the target cells, into different intracellular compartments or (ii) after irradiation the transfer molecule is in contact with the cells for a period of time sufficient to allow its uptake into the cells. Provided the transfer molecule is taken up into different intracellular compartments to the photosensitizing agent, the transfer molecule can be taken up before or after irradiation.

The term "cell" is used herein to include all eukaryotic cells (including insect cells and fungal cells). Representative "cells" thus include all types of mammalian and non-mammalian animal cells, plant cells, insect cells, fungal cells and protozoa.

The methods of the present invention may be used in vitro or in vivo, either by in situ treatment (for example by utilising targetting moieties) or by ex vivo treatment followed by the administration of the treated cells to the body. The methods of the present invention may be used for example in the treatment of cancer. Several photosensitisers accumulate preferentially in neoplastic tissues, the selectivity for a tumor over the surrounding tissue being usually a factor of 2-3, but this factor may in some cases, such as for brain tissues, be higher, i.e. up to 30. Alternatively, a particular photosensitising agent may be targeted to a particular tumor by the methods described above. Furthermore, molecules which may be of clinical interest for treatment of cancer, but are restricted by low or no uptake into the cytosol can be introduced into the cytosol and targetted to specific cells by means of the present invention. Gelonin, as exemplified below, is an example of such a molecule. Other molecules, either alone or linked to other molecules which target the molecule to be internalised to a particular cell (e.g. antibodies, transferrin, photosensitisers, apoB on reconstituted LDL-particles) can be used. The advantage of such a combination treatment would be 1) enhanced cytotoxic effect in deeper layers of the tumor tissues since low and subtoxic doses of light are sufficient for disruption of lysosomes and endosomes; 2) enhanced specificity of the treatment since PCI is only given to the tumour area.

Methods of the invention may also be used for treating various other disorders, as dictated by the selection of the molecule to be introduced into the cell, such as rheumatoid arthritis, artherosclerosis and other cardiovascular diseases, virus and other infections, psoriasis, solar keratosis, wound healing, fracture healing, warts and inherited genetic disorders such as cystic fibrosis, Gorlin's syndrom and ataxia telangiectasia.

The methods of the invention may also be used in gene therapy, i.e. the therapeutic transfer of genes to a patient's cells. Gene therapy is promising as a method for treating many diseases such as cancer, cardiovascular diseases, viral infections, monogenic disorders such as cystic fibrosis and many other conditions such as those described above. One significant problem in gene therapy today is the high efficiency and specificity of gene transfer which must occur in vivo. In current methods many different carriers or vectors are used for achieving gene transfer in gene therapy. As examples polycationic compounds, cationic lipids and viral systems can be mentioned, but so far in vivo gene therapy has met with little success.

Among the many known drawbacks of the current methods are low serum stability of the vector, limited specificity in gene delivery, low efficiency in gene delivery etc. The PCI methods of the present invention provide a means of substantially improving both the efficiency and the specificity of many of the gene delivery methods presently employed in gene therapy, by improving the step of endosomal release which can be efficiency-limiting both for many synthetic gene delivery vectors and for several viral systems. The light treatment inherent in the PCI method also makes it possible to precisely define where in the body the enhanced gene transfer shall occur, since the increase in gene transfer efficiency will only occur in illuminated areas. Transfection may be performed, in vitro, in vivo, or ex vivo (with cells or tissues being administered to the patient as appropriate). Preferably suitable carriers and vectors for transfection include adenoviruses, polycations such as polylysine (e.g. poly-D-lysine or poly-L-lysine), SuperFect®, polyethyleneimine or dendrimers; cationic lipids such as DOTAP or Lipofectin or cationic lipids formulated with a "helper lipid" such as DOPE; peptides and targeted vectors such as e.g. transferrin polylysine or targeted adenovirus vectors. In a preferred embodiment of the invention the carrier used for the therapeutic gene is adenovirus.

Another preferred aspect of the present invention is to use non-viral carrier systems such as for example cationic polymers including peptides and cationic lipids. Typical polymers include for example polyamine, polyaminoacids including basic polyaminoacids, synthetic and natural cationic sugar polymers, methacrylate polymers, dendrimers, polyalkylenemines and other polymers known in the art to be useful in drug delivery; especially polymers useful in gene delivery. Typical compounds useful according to the present invention include polylysine, polyarginine, poly-L-glutamic acid, polyvinylpyridine, chitosan, polyethylenemine, poly(2-dimethylamino)ethyl methacrylate, histones, protamine, poly(L-ornithine), aviden, spermine, spermidine and any derivative thereof. In a preferred aspect of the present invention polymers described herein may be combined with other polymers or combined with other gene delivery systems. Non-viral gene delivery system useful according to the present invention are, for example, described in R. I. Mahato et al in Advances in Genetics (Eds J. C. Hall et al) (1999) 41 95-156. Cationic polymers are further described in M. C. Garnett in Critical Reviews in Therapeutic Drug Carrier Systems (1999), 16, 147-207, K. A. Howard et al in Biochimica et Biophysica Acta (2000), 1475, 245-255, H. K. Nguyen et al in Gene Therapy (2000), 7, 126-138, A. Bragonzi et al in J. Controlled Release (2000), 65, 187-202, S. C. DeSmedt et al in Pharmaceutical Reseach (2000), 17, 113-126 and R. I. Mahoto in J. Drug Targeting (1999), 7, 249-268.

Another aspect of the present invention involves the use of liposomes or other lipid based constructs as non-viral carrier systems. The liposomes may be pH-sensitive liposomes or non-pH sensitive liposomes. pH-sensitive liposomes consist of at least one pH-sensitive component in the liposome membrane. Typical compounds include fatty acids such as oleic acid, palmitoylhomocysteine, cholesterol, hemisuccinate morpholine salt and dieloylsuccinylglyecerol. In addition to the pH-sensitive components, the liposomes may consist of dioleoylphosphatidylethanolamine (DOPE) and/or other similar phospholipids.

The liposomes or other lipid based delivery system contain preferably at least one cationic lipid.

The lipid-based delivery system may be present in various types of aqueous formulation. Various terms are used for these formulations in the literature: multilamellar liposomes, unilamallar liposomes, pH-sensitive liposomes, nanoemulsions, nanoparticles, proteoliposomes, virosomes, chimerasomes, cochelates, Lipofectin® and lipoplex. References to the use of cationic lipids in gene transfer include P. L. Felgner et al in Proc. Natl. Acad. Sci. USA (1987), 84, 7413-7417, D. D. Lasic et al in Adv. Drug Del Rev (1996), 20, 221-266. L. G. Barron et al in Gene Therapy (1999), 6 1179-1183, S. Kawakami et al in Pharmaceutical Research (2000), 17, 306-313. N. S. Templeton et al in Molecular Biotechnology (1999), 11, 175-180, Y. Zou et al in Cancer Gene Therapy (2000), 7, 683-696, D. D. Stuart et al in Biochemistry et Biophysica Acta (2000), 1463, 219-229, R. I. Mahato et al in Drug Deliv (1997) 4 151 and R. J. Lee et al in Crit. Rev Drug Carrier Syst (1997), 14, 173.

Lipids useful according to the present invention are, for example described in U.S. Pat. No. 6,120,751, U.S. Pat. No. 6,056,938, U.S. Pat. No. 6,093,816, U.S. Pat. No. 6,039,936, U.S. Pat. No. 6,034,137, U.S. Pat. No. 6,034,135, U.S. Pat. No. 6,020,526, U.S. Pat. No. 5,980,935, U.S. Pat. No. 5,958,935, U.S. Pat. No. 5,935,936, U.S. Pat. No. 5,877,220, U.S. Pat. No. 5,830,430, U.S. Pat. No. 5,777,153, U.S. Pat. No. 5,705,693, U.S. Pat. No. 5,459,127, U.S. Pat. No. 5,334,761, U.S. Pat. No. 5,264,618 and references therein.

Typical examples of cationic lipids include N [1-(2,3-dioleyloxy)propyl-N,N,N-trimethyl-ammonium chloride (DOTMA), 1,2-dimyristyl-oxypropyl-3-dimethylhydroxyethylammonium bromide (DMRIE), 1,2-bis(oleoyloxy)-3-(trimethylammino)propane (DOTAP), 3β(N',N'-dimethylaminoethane)-carbamoyl-cholesterol (DC-Chol), 2,3-dioleyl-oxy-N [2-sperminecarboxyyl-amido]ethyl-N,N-dimethyl-1-propanaminium trifluoracetate (DOS PA), 3-β ($N^4$-spermine carbamoyl)-cholesterol, 3-β ($N^4$-spermidine carbamoyl)-cholesterol and diooctadecylamidoglyl spermine (DOGS).

As described above, in one of the preferred embodiments of the invention the carrier is cationic lipids. It has earlier been reported that photochemical treatment has an inhibiting effect on transfection mediated by cationic lipids when light is given after the transfer molecule (Prasmickaite et al. (2000), J. Gene Med. 6, in press). However, it has now very surprisingly been shown that when light is given before the transfer molecule PCI can have a stimulating effect on transfection by cationic lipids (see Example 9).

Thus, a further aspect of the invention provides compositions comprising a transfer molecule and a photosensitizing agent for use in therapy. Optionally the transfer molecule and/or the photosensitizing agent in the compositions may be associated with carrier molecules such as those described above. Preferably the compositions are used for cancer therapy or gene therapy. For gene therapy a preferred carrier molecule is adenovirus. Other preferred carriers are cationic lipids.

In a further aspect therefore the present invention provides the use of a transfer molecule and/or a photosensitizing agent as described herein for the preparation of a medicament for use in therapy, wherein said photosensitizing agent and separately said transfer molecule is contacted with cells or tissues of a patient and said cells are irradiated with light of a wavelength effective to activate the photosensitizing agent and irradiation is performed prior to the cellular uptake of said transfer molecule into an intracellular compartment containing said photosensitizing agent, preferably prior to cellular uptake of said transfer molecule into any intracellular compartment. Methods of treatment comprising such methods form alternative aspects of the invention.

Thus, the invention provides a method of treating or preventing a disease, disorder or infection in a patient comprising introducing a transfer molecule into one or more cells in vitro, in vivo or ex vivo according to the method as described hereinbefore and where necessary (ie. when transfection is conducted in vitro or ex vivo) administering said cells to said patient.

As defined herein "treatment" refers to reducing, alleviating or eliminating one or more symptoms of the disease, disorder or infection which is being treated, relative to the symptoms prior to treatment. "Prevention" refers to delaying or preventing the onset of the symptoms of the disease, disorder or infection.

As mentioned previously, such methods also have application in methods of vaccination. Accordingly, a further aspect of the invention provides a method of expressing or presenting an antigenic molecule (the transfer molecule) or a part thereof on the surface of a cell, preferably an antigen-presenting cell, wherein said method comprises the steps as defined hereinbefore.

As used herein "expressing" or "presenting" refers to the presence of the molecule or a part thereof on the surface of said cell such that at least a portion of that molecule is exposed and accessible to the environment surrounding that cell. Expression on the "surface" may be achieved in which the molecule to be expressed is in contact with the cell membrane and/or components which may be present or caused to be present in that membrane.

This method may be performed in vitro or in vivo. Preferably however, such antigenic presentation may advantageously result in the stimulation of an immune response, preferably an immune response which confers protection against subsequent challenge by an entity comprising or containing said antigen molecule or part thereof, and consequently the invention finds particular utility as a method of vaccination. Preferably therefore, the present invention provides a method of vaccination comprising the method described hereinbefore.

In this aspect of the invention, the transfer molecule as defined herein is referred to as an "antigenic molecule". The antigenic molecule may be any molecule wherein that molecule or a part thereof is capable of stimulating an immune response, when presented to the immune system in an appropriate manner. Advantageously, therefore the antigenic molecule will be a vaccine antigen or vaccine component, such as a polypeptide containing entity.

Many such antigens or antigenic vaccine components are known in the art and include all manner of bacterial or viral antigens or indeed antigens or antigenic components of any pathogenic species including protozoa or higher organisms. Whilst traditionally the antigenic components of vaccines have comprised whole organisms (whether live, dead or attenuated) i.e. whole cell vaccines, in addition sub-unit vaccines, ie. vaccines based on particular antigenic components of organisms e.g. proteins or peptides, or even carbohydrates, have been widely investigated and reported in the literature. Any such "sub-unit"-based vaccine component may be used as the antigenic molecule of the present invention. However, the invention finds particular utility in the field of peptide vaccines. Thus, a preferred antigenic molecule according to the invention is a peptide (which is defined herein to include peptides of both shorter and longer lengths i.e. peptides, oligopeptides or polypeptides, and also protein molecules or fragments thereof e.g. peptides of 5-500 e.g. 10 to 250 such as 15 to 75, or 8 to 25 amino acids). Parts of antigenic molecules which are presented or expressed preferably comprise parts which are generated by antigen-processing machinery within the cell. Parts may however be generated by other means which may be achieved through appropriate antigen design (e.g. pH sensitive bands) or through other cell processing means. Conveniently such parts are of sufficient size to generate an immune response, e.g. in the case of peptides greater than 5, e.g. greater than 10 or 20 amino acids in size.

A vast number of peptide vaccine candidates have been proposed in the literature, for example in the treatment of viral diseases and infections such as AIDS/HIV infection or influenza, canine parvovirus, bovine leukaemia virus, hepatitis, etc. (see e.g. Phanuphak et al., Asian Pac. J. Allergy. Immunol. 1997, 15(1), 41-8; Naruse, Hokkaido Igaku Zasshi 1994, 69(4), 811-20; Casal et al., J. Virol., 1995, 69(11), 7274-7; Belyakov et al., Proc. Natl. Acad. Sci. USA, 1998, 95(4), 1709-14; Naruse et al., Proc. Natl. Sci. USA, 1994 91(20), 9588-92; Kabeya et al., Vaccine 1996, 14(12), 1118-22; Itoh et al., Proc. Natl. Acad. Sci. USA, 1986, 83(23) 9174-8. Similarly bacterial peptides may be used, as indeed may peptide antigens derived from other organisms or species.

In addition to antigens derived from pathogenic organisms, peptides have also been proposed for use as vaccines against cancer or other diseases such as multiple sclerosis. For example, mutant oncogene peptides hold great promise as cancer vaccines acting an antigens in the simulation of cytotoxic T-lymphocytes. (Schirrmacher, Journal of Cancer Research and Clinical Oncology 1995, 121, 443-451; Curtis Cancer Chemotherapy and Biological Response Modifiers, 1997, 17, 316-327). A synthetic peptide vaccine has also been evaluated for the treatment of metastatic melanoma (Rosenberg et al., Nat. Med. 1998, 4(3), 321-7). A T-cell receptor peptide vaccine for the treatment of multiple sclerosis is described in Wilson et al., J. Neuroimmunol. 1997, 76(1-2), 15-28. Any such peptide vaccine component may be used as the antigenic molecule of the invention, as indeed may any of the peptides described or proposed as peptide vaccines in the literature. The peptide may thus be synthetic or isolated or otherwise derived from an organism.

The cell which is subjected to the methods, uses etc. of this aspect of the invention may be any cell which is capable of expressing, or presenting on its surface a molecule which is administered or transported into its cytosol.

Since the primary utility of this aspect of the invention resides in antigen-presentation or vaccination, the cell is conveniently an immune effector cell i.e. a cell involved in the immune response. However, other cells may also present antigen to the immune system and these also fall within the scope of this aspect of the invention. The cells according to this aspect are thus advantageously antigen-presenting cells. The antigen-presenting cell may be involved in any aspect or "arm" of the immune response, including both humoral and cell-mediated immunity, for example the stimulation of antibody production, or the stimulation of cytotoxic or killer cells, which may recognise and destroy (or otherwise eliminate) cells expressing "foreign" antigens on their surface. The term "stimulating an immune response" thus includes all types of immune responses and mechanisms for stimulating them.

The stimulation of cytotoxic cells or antibody-producing cells, requires antigens to be presented to the cell to be stimulated in a particular manner by the antigen-presenting cells, for example MHC Class I presentation (e.g. activation of $CD8^+$ cytotoxic T-cells requires MHC-1 antigen presentation)

Antigen-presenting cells are known in the art and described in the literature and include for example, lymphocytes (both T and B cells), dendritic cells, macrophages etc. Others include for example cancer cells e.g. melanoma cells.

For antigen presentation by an antigen-presenting cell to a cytotoxic T-cell (CTL) the antigenic molecule needs to enter the cytosol of the antigen-presenting cell (Germain, Cell, 1994, 76, 287-299). The present invention provides an efficient means of delivery of the antigenic molecule into the cytosol.

Once released in the cell cytosol by the photochemical internalisation process, the antigenic molecule may be processed by the antigen-processing machinery of the cell and presented on the cell surface in an appropriate manner e.g. by Class I MHC. This processing may involve degradation of the antigen, e.g. degradation of a protein or polypeptide antigen into peptides, which peptides are then complexed with molecules of the MHC for presentation. Thus, the antigenic molecule expressed or presented on the surface of the cell according to the present invention may be a part or fragment of the antigenic molecule which is taken up in the cell.

Antigens may be taken up by antigen-presenting cells by endocytosis and degraded in the endocytic vesicles to peptides. These peptides may bind to MHC class II molecules in the endosomes and be transported to the cell surface where the peptide-MHC class II complex may be recognised by CD4+ T helper cells and induce an immune response. Alternatively, proteins in the cytosol may be degraded into parts thereof, e.g. by proteasomes and transported into endoplasmic reticulum by means of TAP (transporter associated with antigen presentation) where the peptides may bind to MHC class I molecules and be transported to the cell surface as illustrated in the FIG. 1 (Yewdell and Bennink, 1992, Adv. Immunol. 52: 1-123). If the peptide is of foreign antigen origin, the peptide-MHC class I complex will be recognised by CD8+ cytotoxic T-cells (CTLs). The CTLs will bind to the peptide-MHC(HLA) class I complex and thereby be activated, start to proliferate and form a clone of CTLs. The target cell and other target cells with the same peptide-MHC class I complex on the cells surface may be killed by the CTL clone. Immunity against the foreign antigen may be established if a sufficient amount of the antigen can be introduced into the cytosol (Yewdell and Bennink, 1992, supra; Rock, 1996, Immunology Today 17: 131-137). This is the basis for development of inter alia cancer vaccines. One of the largest practical problems is to introduce sufficient amounts of antigens (or parts of the antigen) into the cytosol. This may be solved according to the present invention by PCI.

Compositions of the present invention may also comprise a cell containing a transfer molecule which has been internalised into the cytosol of said cell by a method of the invention, for use in therapy, particularly cancer therapy, gene therapy and vaccination.

Thus, a yet further aspect of the invention provides a cell or a population of cells containing a transfer molecule which has been internalised into the cytosol of said cell, which cell is obtainable by a method of the present invention.

A yet further aspect of the invention provides the use of a such a cell or population of cells for the preparation of a composition or a medicament for use in therapy, preferably cancer therapy, gene therapy or vaccination.

The invention further provides a method of treatment of a patient comprising administering to said patient cells or compositions of the present invention, ie. a method comprising the steps of introducing a molecule into a cell as described hereinbefore and administering said cell thus prepared to said patient. Preferably said methods are used to treat cancer, in gene therapy or for vaccination.

In vivo, any mode of administration common or standard in the art may be used, e.g. injection, infusion, topical administration, both to internal and external body surfaces etc. For in vivo use, the invention can be used in relation to any tissue which contains cells to which the photosensitising agent and the transfer molecule are localized, including body fluid locations, as well as solid tissues. All tissues can be treated as long as the photosensitiser is taken up by the target cells, and the light can be properly delivered.

Thus, the compositions of the invention may be formulated in any convenient manner according to techniques and procedures known in the pharmaceutical art, e.g. using one or more pharmaceutically acceptable carrier or excipients. "Pharmaceutically acceptable" as referred to herein refers to ingredients that are compatible with other ingredients of the compositions as well as physiologically acceptable to the recipient. The nature of the composition and carriers or excipient materials, dosages etc. may be selected in routine manner according to choice and the desired route of administration, purpose of treatment etc. Dosages may likewise be determined in routine manner and may depend upon the nature of the molecule, purpose of treatment, age of patient, mode of administration etc. In connection with the photosensitizing agent the potency/ability to disrupt membranes on irradiation, should also be taken into account.

The invention will now be described in more detail in the following non-limiting Examples with reference to the following drawings in which.

A. I. The photosensitizer S is endocytosed (I) and ends up in intracellular vesicles (II). These vesicles rupture upon exposure to light (III).

B. After the photochemical treatment as described in A the cells are treated with a molecule M which is endocytosed and ends up in intracellular vesicles. These vesicles will fuse with photochemically damaged vesicles and the molecule M will be released into the cytosol.

Figure 8:
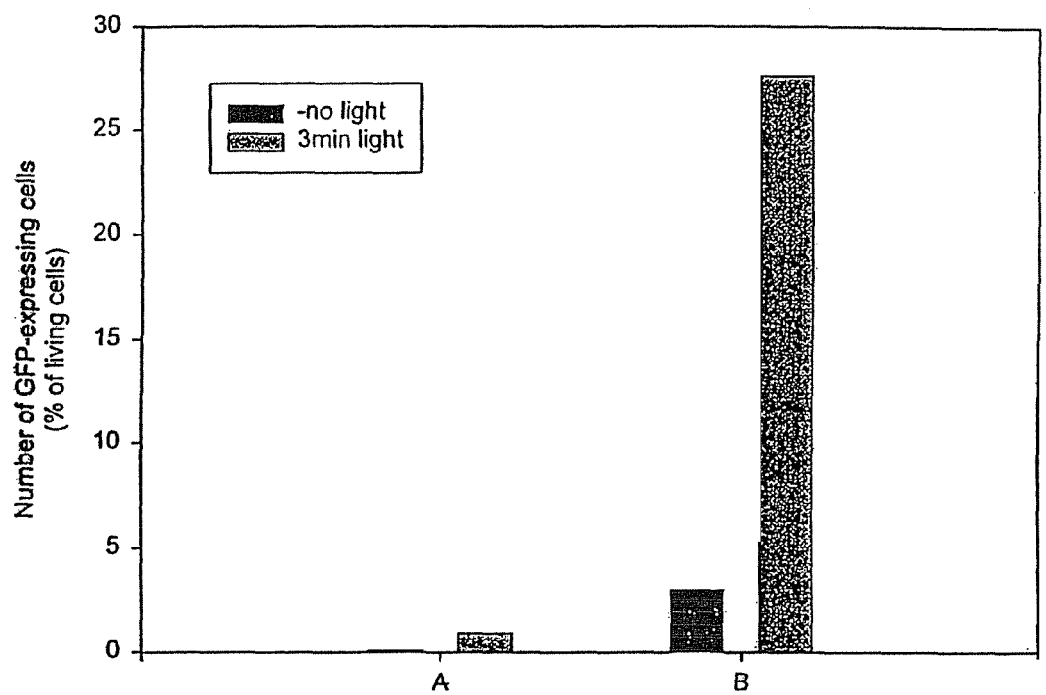

FIG. 8 shows the effect on transfection of treatment of the cells at 0° C. with the pEGFP-N1 polylysine complex.

Figure 9:
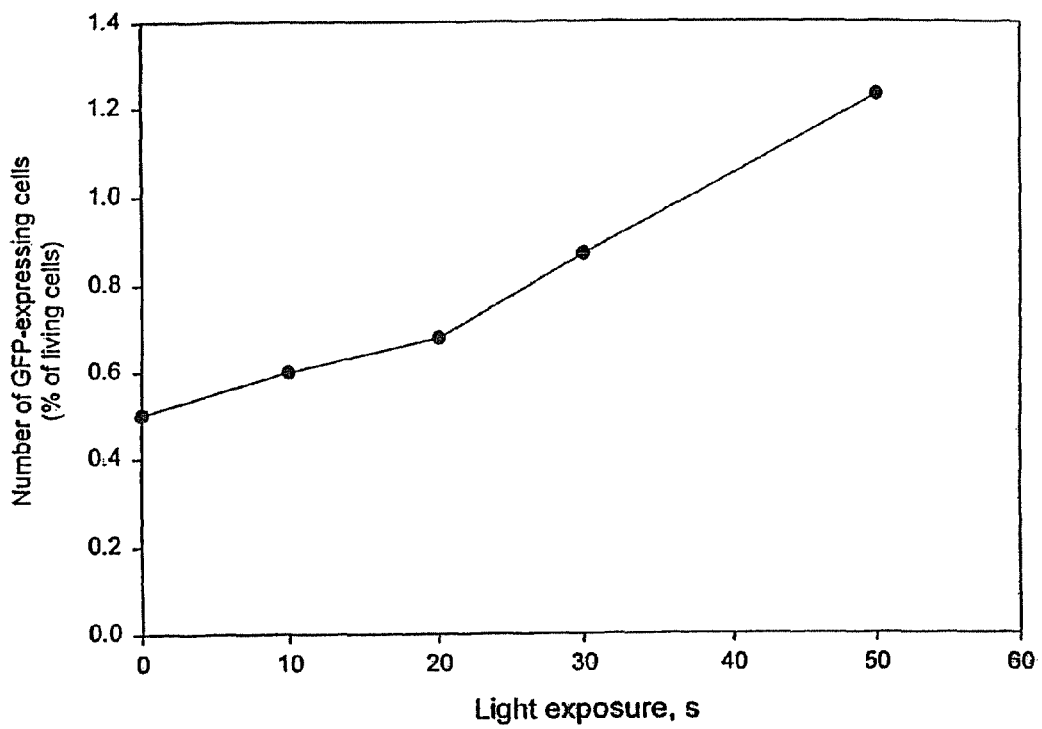

FIG. 9 shows light-induced transfection of pEGFP-N1 polylysine complex when 3-THPP, which is mainly not localised in endocytoxic vesicles, is used as a photosensitizing agent.

Figure 10:
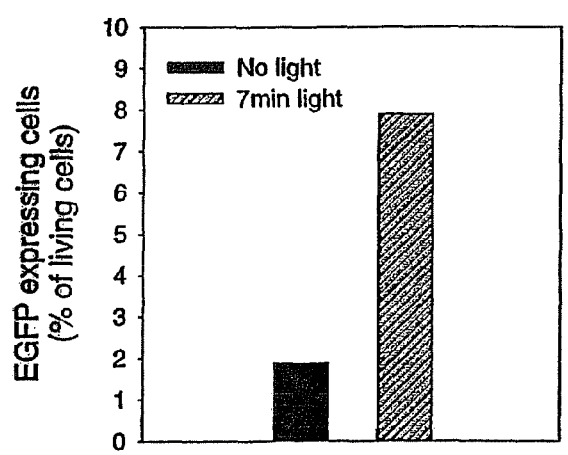

FIG. 10 shows the effect of a combination of photosensitizer and light pretreatment on the transfection of cells with cationic lipids.

Figure 11:
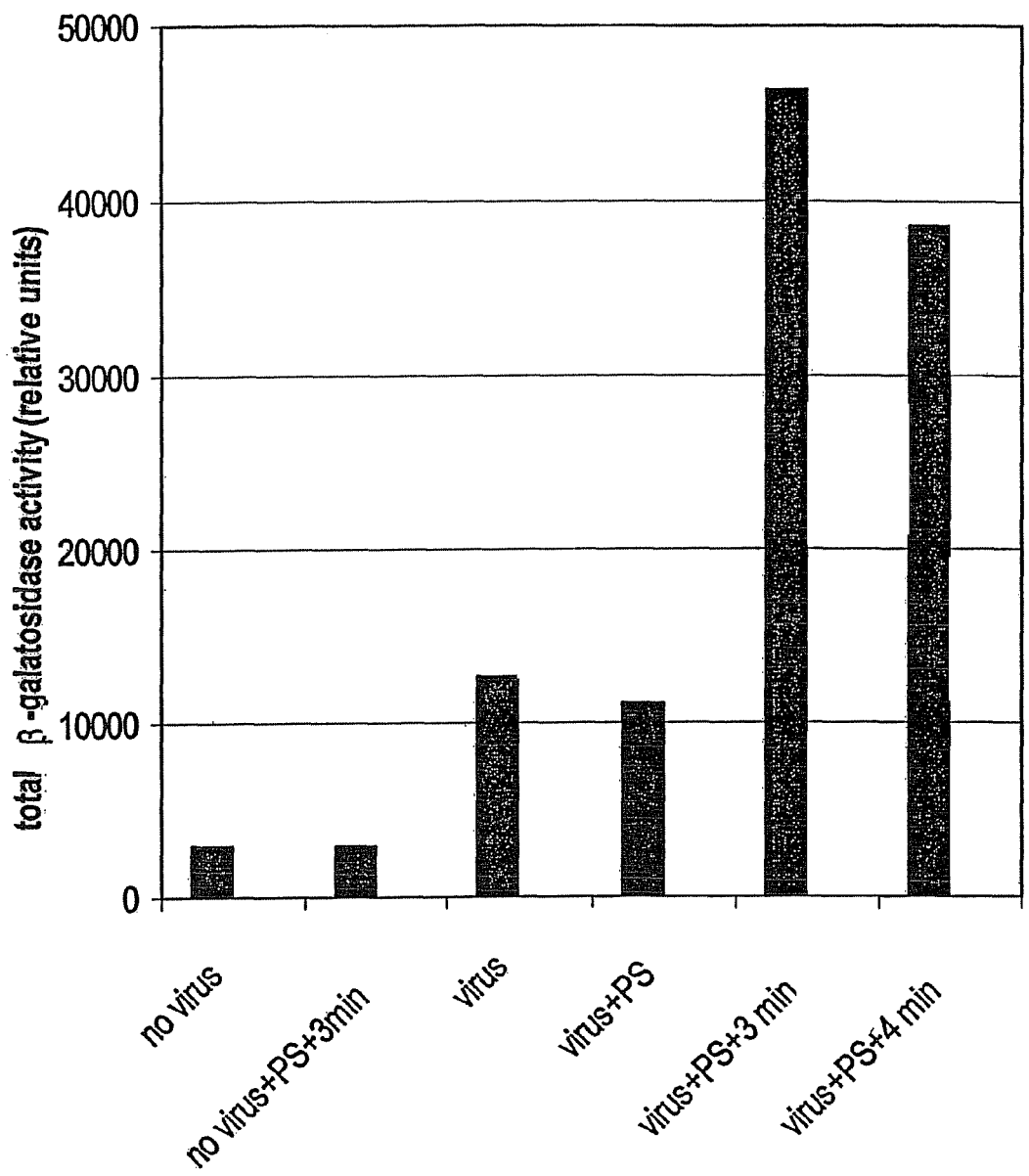

FIG. 11 shows the effect of photochemical treatment on adenovirus transduction of THX cells.

Figure 12:
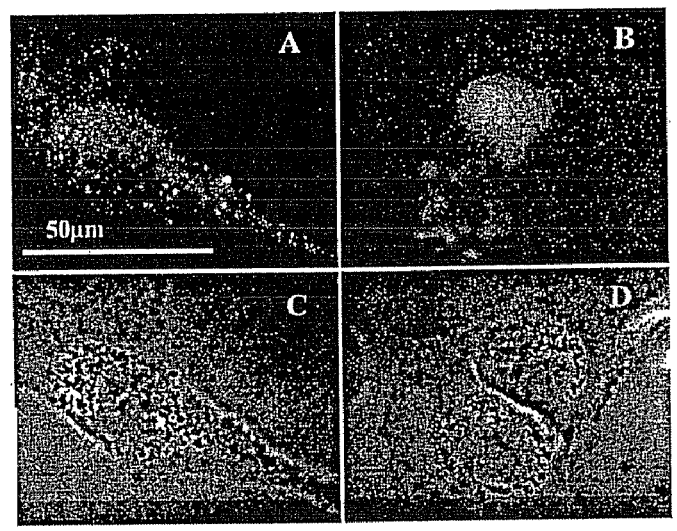

FIG. 12 shows the effect of photochemical treatment on intracellular localisation of FITC-dextran. THX cells were incubated with 20 μg/ml $AlPcS_{2a}$ for 18 h followed by 4 h incubation in $AlPcS_{2a}$-free medium. Then the cells were either exposed to light for 4 min (B,D) or kept in the darkness (A,C) before a 3 h incubation with 5 mg/ml FITC-dextran. Fluorescence (A,B) and phase contrast (C,D) micrographs.

Figure 13:
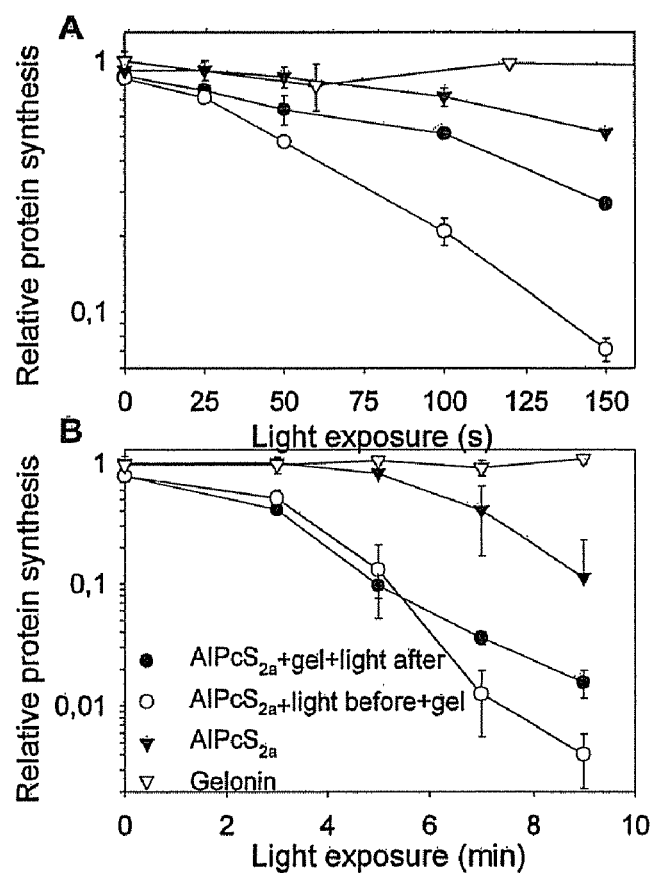

FIG. 13 shows the effect of photochemical treatment on gelonin toxicity in THX and HCT 116 cells. For the "light before" strategy, the cells were first incubated with 20 μg/ml $AlPcS_{2a}$ for 18 h, then for another 4 h in $AlPcS_{2a}$-free medium before exposure to light as indicated in the figure. After illumination 1 μg/ml gelonin was added, and the cells were incubated for 18 h. For the "light after" strategy the cells were co-incubated with 20 μg/ml $AlPcS_{2a}$ and 1 μg/ml gelonin for 18 h before exposure to light as indicated in the figure. The control cells were treated only with 1 μg/ml gelonin for 18 h and exposed to light; or only with 20 μg/ml $AlPcS_{2a}$ for 18 h, chased 4 h in $AlPcS_{2a}$-free medium and exposed to light. [$^3$H]-leucine incorporation into proteins was measured the next day after light treatment and expressed as relative protein synthesis. Data points represent mean±standard error (S.E.) of triplicates.

Figure 14:
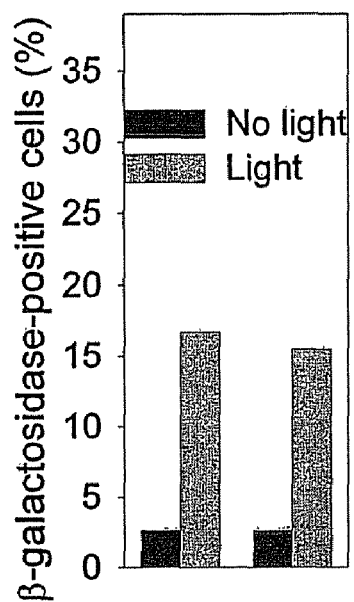

FIG. 14 shows the effect of photochemical treatment on expression of β-galactosidase in THX cells infected with AdHCMV-lacZ. For the "light before" strategy $AlPcS_{2a}$-pretreated cells were incubated for another 4 h in $AlPcS_{2a}$-free medium before light exposure for 3 min. Following illumination the cells were infected with AdHCMV-lacZ (at MOI 1) for 30 min at 37° C. Then 2 ml of medium was added and the cells were incubated for two days before analysis of β-galactosidase expression. For the "light after" strategy $AlPcS_{2a}$-treated cells were incubated in $AlPcS_{2a}$-free medium for 3 h before a 30 min infection with AdHCMV-lacZ. After addition of 2 ml of culture medium the cells were incubated for another 30 min before illumination for 3 min, and two days later were analysed for β-galactosidase expression.

Figure 15:
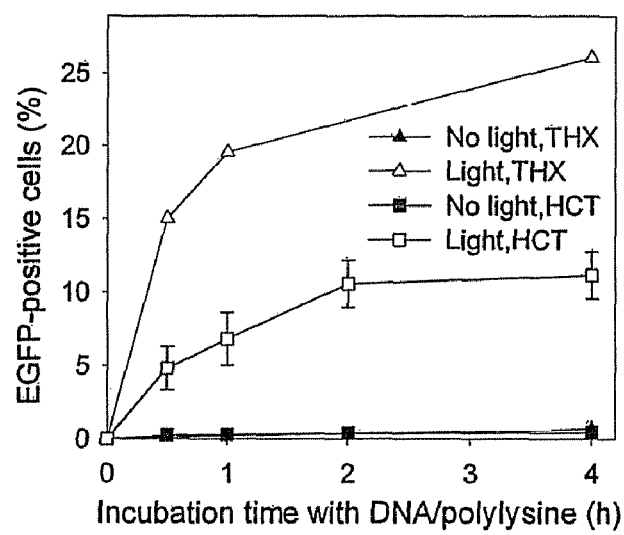

FIG. 15 shows the effect of the incubation time on the efficiency of light-induced transfection with pEGFP/polylysine in THX and HCT 116 cells. $AlPcS_{2a}$-pretreated cells were washed and incubated in $AlPcS_{2a}$-free medium for 4 h before light exposure for 3 min (THX cells) or 7 min (HCT) cells. Following illumination the pEGFP-N1/polylysine complex (5 μg/ml plasmid) was added, and the cells were incubated for different time periods indicated in the figure. After removing the complex fresh complex-free medium was added and the cells were incubated for two days before analysis of EGFP expression.

Figure 16:
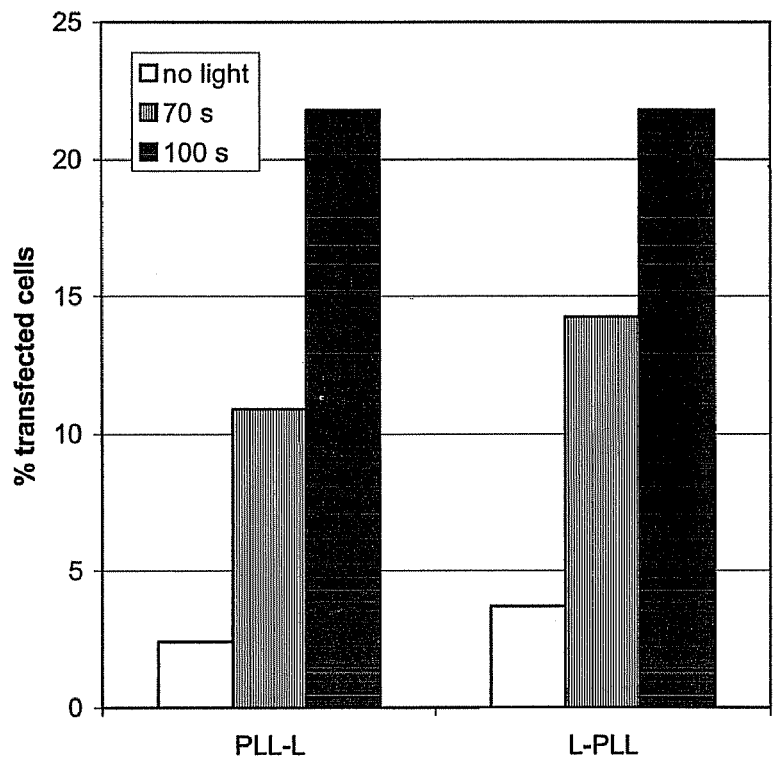

FIG. 16 shows the effect of the light first PCI strategy on transfection of THX cells mediated by poly-L-lysine using $TPPS_{2a}$ as the photosensitiser compared to the light after strategy, using various irradiation times. PLL-L: Irradiation after the pEGFP-N1/PLL complex. L-PLL: Irradiation before the pEGFP-N1/PLL complex. Unshaded bars—no light, shaded bars—70 seconds irradiation, solid bars—100 seconds irradiation.

Figure 17:
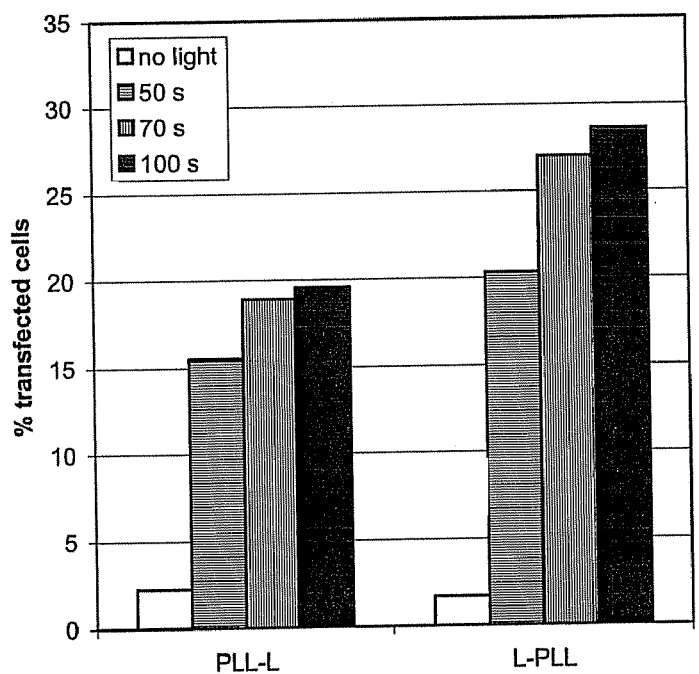

FIG. 17 shows the effect of the light first PCI strategy on transfection of THX cells mediated by poly-L-lysine using $TPPS_4$ as the photosensitiser compared to the light after strategy, using various irradiation times. PLL-L: Irradiation after the pEGFP-N1/PLL complex. L-PLL: Irradiation before the pEGFP-N1/PLL complex. Unshaded bars—no light, horizontally shaded bars—50 seconds irradiation, vertically shaded bars—70 seconds irradiation, solid bars—100 seconds irradiation.

Figure 18:
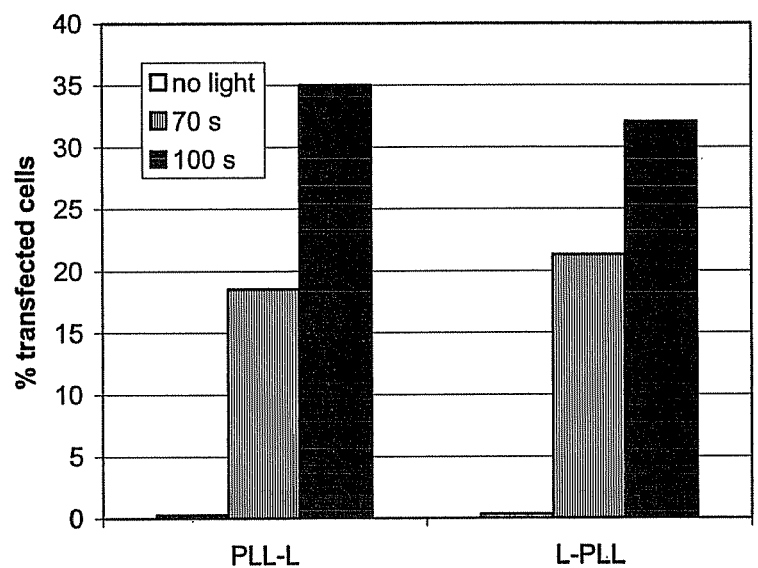

FIG. 18 shows the effect of the light first PCI strategy on transfection of HCT 116 cells mediated by poly-L-lysine, using $TPPS_{2a}$ as the photosensitiser compared to the light after strategy, using various irradiation times. PLL-L: Irradiation after the PEGFP-N1/PLL complex. L-PLL: Irradiation before the pEGFP-N1/PLL complex. Unshaded bars—no light, shaded bars—70 seconds irradiation, solid bars—100 seconds irradiation.

Figure 19:
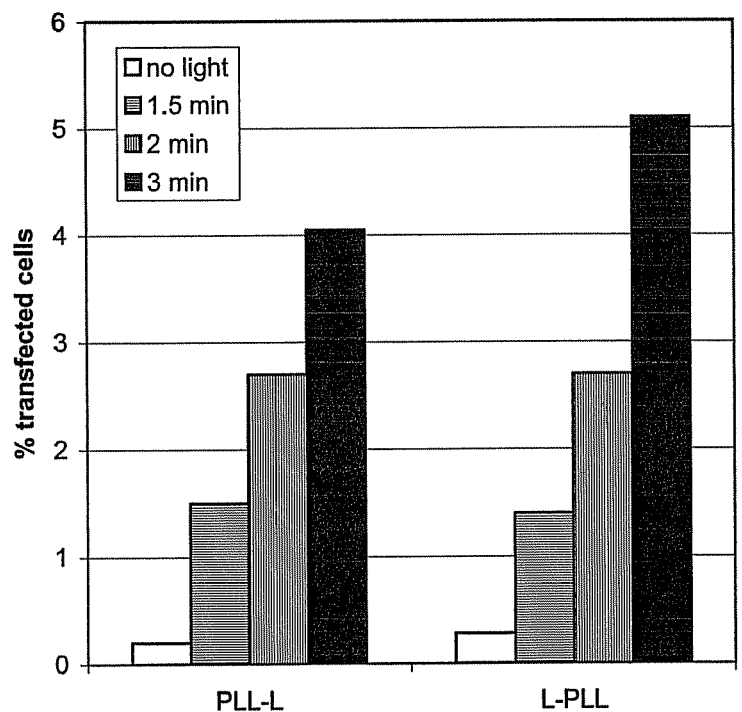

FIG. 19 shows the effect of the light first PCI strategy on transfection of HCT 116 cells mediated by poly-L-lysine, using $TPPS_4$ as the photosensitiser. PLL-L: Irradiation after the pEGFP-N1/PLL complex. L-PLL: Irradiation before the pEGFP-N1/PLL complex. Unshaded bars—no light, horizontally shaded bars—1.5 minutes irradiation, vertically shaded bars—2 minutes irradiation, solid bars—3 minutes irradiation.

Figure 20:
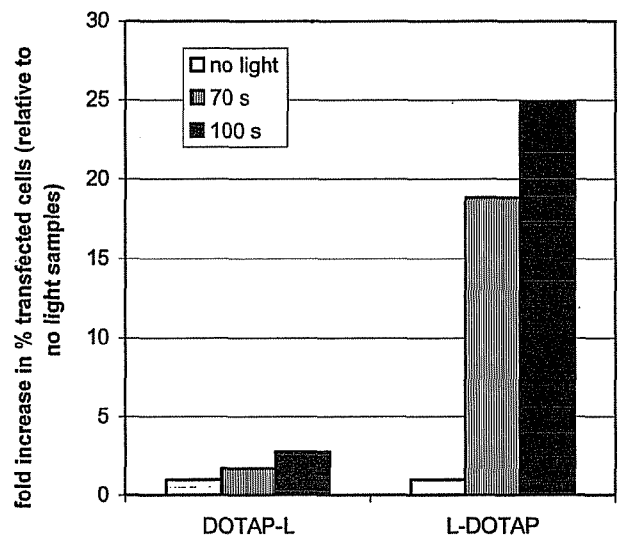

FIG. 20 shows the effect of the light first PCI strategy on transfection mediated by DOTAP using $TPPS_4$ as the photosensitiser compared to the light after strategy, using various irradiation times. DOTAP-L: Irradiation after the pEGFP-N1/DOTAP complex. L-DOTAP: Irradiation before the pEGFP-N1/DOTAP complex. Unshaded bars—no light, shaded bars—70 seconds irradiation, solid bars—100 seconds irradiation.

Figure 21:
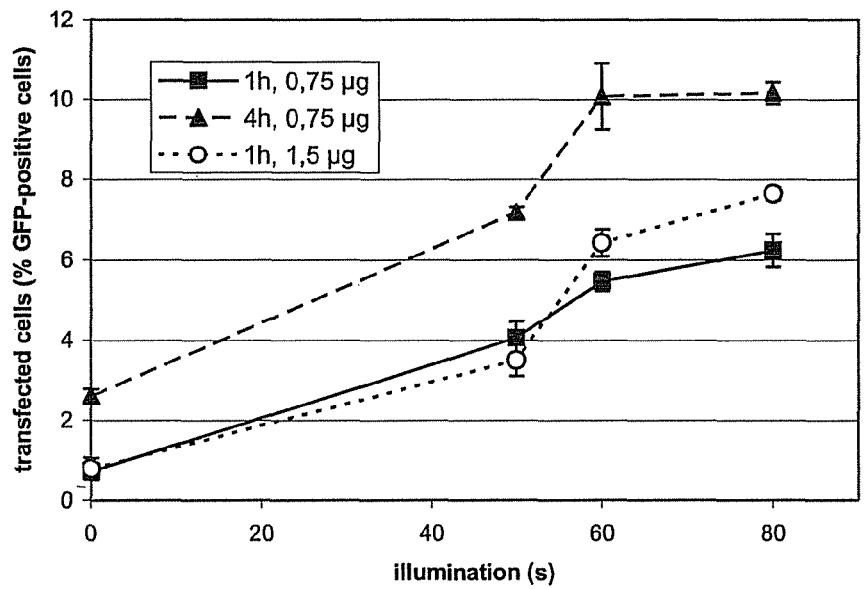

FIG. 21 shows the effect of the light first PCI strategy on transfection mediated by SuperFect® using $TPPS_{2a}$ as the photosensitiser, where various illumination and transfection times are used and the amount of DNA for transfection varied. ■—transfection for 1 hour with 0.75 µg DNA; ∆—transfection for 4 hours with 0.75 µg DNA; ○—transfection for 1 hour with 1.5 µg DNA.

Figure 22:
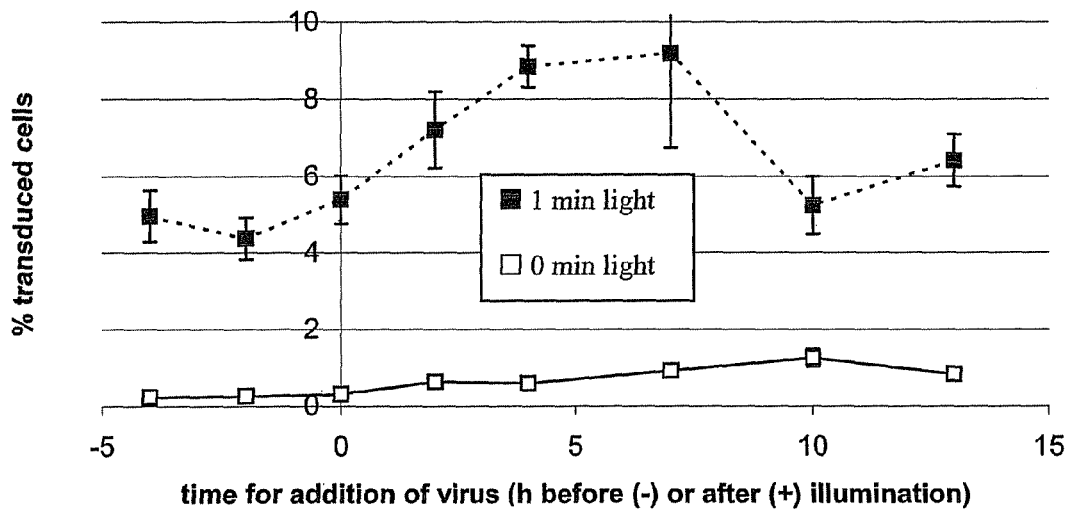

FIG. 22 shows the effect of the light first PCI strategy on adenovirus mediated gene transduction of HCT 116 cells using $AlPcS_{2a}$ as the photosensitiser, in which the virus is added at various times. The percentage of transduced cells when virus was added at different time points was analysed by flow cytometry as described in the Example. The time points of addition of the virus complexes are indicated on the figure. Time points to the left of the Y-axis represent virus added before irradiation, time points to the right represent addition of virus after irradiation. ■—1 minute irradiation; □—no irradiation.

Figure 23:
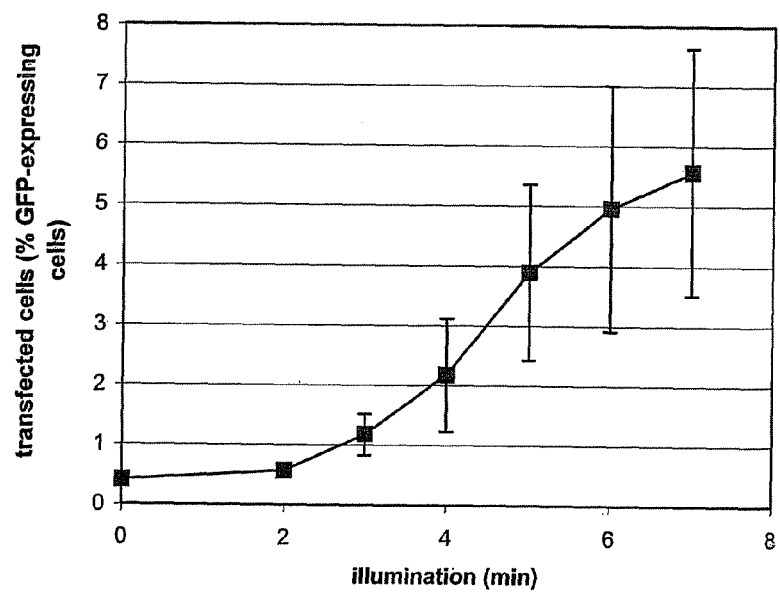

FIG. 23 shows the effect of the light first PCI strategy on transfection of HCT 116 cells mediated by Poly-D-lysine using $AlPcS_{2a}$ as the photosensitiser, with variable irradiation times.

Figure 24:
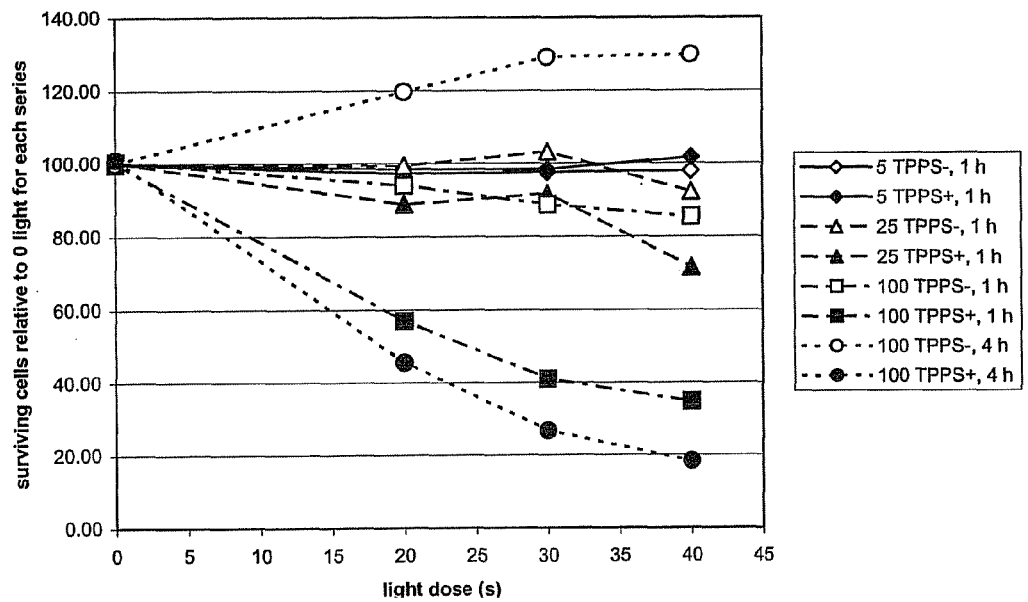

FIG. 24 shows the effect of the light first PCI strategy on cell killing by the cytostatic agent bleomycin using $TPPS_{2a}$ as the photosensitiser, with variable amounts of bleomycin, irradiation times and transfection times. ◇—5 TPPS−, 1 h=5 µM bleomycin, without $TPPS_{2a}$, 1 h incubation; ◆—5 TPPS+, 1 h=5 µM bleomycin, with $TPPS_{2a}$, 1 h incubation; __—25 TPPS−, 1 h=25 µM bleomycin, without $TPPS_{2a}$, 1 h incubation; ▲—25 TPPS+, 1 h=25 µM bleomycin, with $TPPS_{2a}$, 1 h incubation; □—100 TPPS−, 1 h=100 µM bleomycin, without $TPPS_{2a}$, 1 h incubation; ■—100 TPPS+, 1 h=100 µM bleomycin, with $TPPS_{2a}$, 1 h incubation; ○—100 TPPS−, 4 h=100 µM bleomycin, without $TPPS_{2a}$, 4 h incubation; ●—100 TPPS+, 4 h=100 µM bleomycin, with $TPPS_{2a}$, 4 h incubation.

Figure 25:
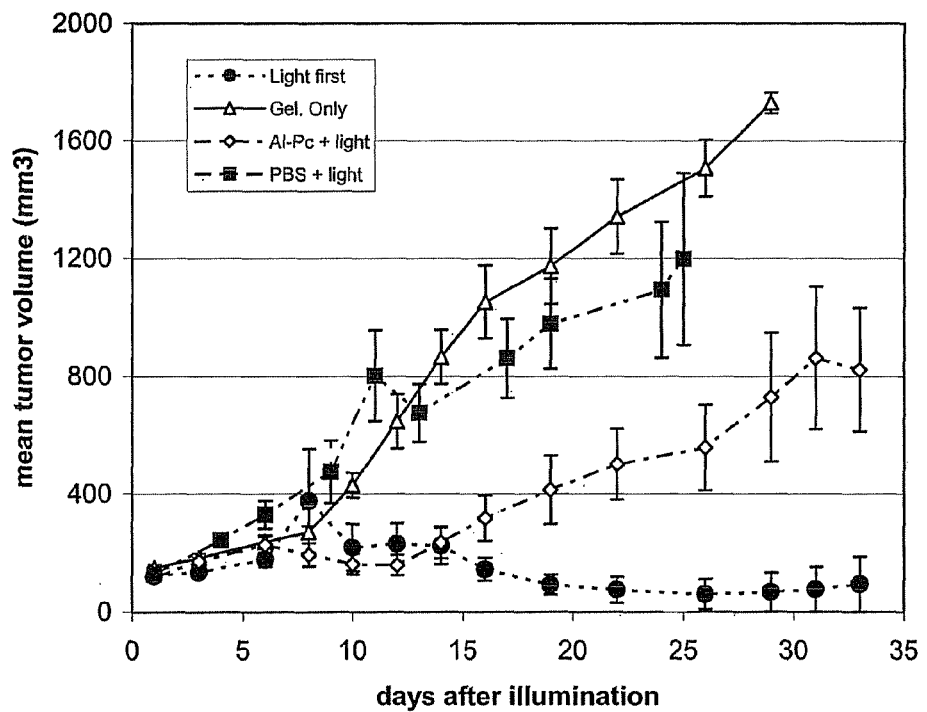

FIG. 25 shows the effect of PCI with gelonin for treatment of tumours in a mouse in vivo model. The treatment groups were as follows: (_) gelonin only; (■) a placebo treatment of phosphate buffered saline (PBS) injection combined with illumination; (◆) only the photochemical treatment (i.e. $AlPcS_{2a}$+light), but no gelonin; (●) full gelonin PCI treatment (i.e. $AlPcS_{2a}$+gelonin+light).

EXAMPLES

Materials and Methods

Cell Lines

The human melanoma cell line THX was established from tumour tissue obtained from a patient treated for metastatic malignant melanoma at the Norwegian Radium Hospital (Aamdal et al., 1986., Int. J. Cancer, 37, 579), and grown in RMPI 1640 (Gibco-BRL) supplemented with 10% FCS (Gibco-BRL) and 2 mM glutamine (Gibco-BRL). The human colon carcinoma cell line HCT 116 was obtained from American Type Culture Collection (ATCC no. CCL-247) and grown in RPMI 1640 medium supplemented with 10% foetal calf serum, 100 U/ml penicillin, 100 mg/ml streptomycin and 2 mM glutamine (all Gibco BRL, Paisley, UK).

Irradiation

Two different light sources were used for treatment of the cells, both consisting of a bank of 4 fluorescent tubes. Cells treated with $TPPS_4$, $TPPS_{2a}$, and 3-THPP (Porphyrin Products, Logan, Utah) were exposed to blue light (model 3026; Appl. Photophysics, London, UK) with a light intensity reaching the cells of 1.5 $mW/cm^2$ while cells treated with $AlPcS_{2a}$ (Porphyrin Products, Logan, Utah) were exposed to red light (Philips TL 20W/09) filtered through a Cinemoid 35 filter with a light intensity reaching the cells of 1.35 $mW/cm^2$.

Fluorescence Microscopy

The cells were analysed by fluorescence microscopy as described in Berg. K., et al., Biochem. Biophys. Acta., 1370: 317-324, 1998. For analysis of fluorescein-labelled molecules the microscope was equipped with a 450-490 nm excitation filter, a 510 nm dichroic beam splitter and a 510-540 nm band pass emission filter.

Preparation of Plasmid-Plys Complexes and Treatment of cells

Plasmid-pLys complexes (charge ratio, 1.7 as described in Berg et al. (1999) Cancer Res. 59: 1180-83) were prepared by gently mixing 5 µg plasmid (pEGFP-N1; Clontech Laboratories, Inc., Palo Alto, Calif.) in 75 µl of HBS with 5.3 µg pLys (MW 20700; Sigma, St. Louis, Mo.) in 75 µl of HBS. The solutions were incubated for 30 min at room temperature, diluted with culture medium and added to the cells.

THX cells were incubated with 20 µg/ml $AlPcS_{2a}$ for 18 hours at 37° C., washed and incubated in sensitizer-free medium for 3 hours before incubation with plasmid-pLys complexes for 1 hour followed by exposure to light. Alternatively, after the $AlPcS_{2a}$ incubation the cells were washed and incubated in sensitizer free medium for 4 hours before exposure to light followed by a 1 hour incubation with the plasmidpLys complexes. The cells were incubated at 37° C. for 2 days, before analysis of GFP expression was carried out by flow cytometry.

HCT-116 cells were incubated with 20 μg/ml AlPcS$_{2a}$ for 18 hours, washed incubated for 4 hours in the absence of AlPcS$_{2a}$ before light exposure. The cells were treated with pEGFP-N1 polylysine complex for 4 hours immediately before or after exposure to light. After 2 days incubation at 37° C. the GFP expression was studied by flow cytometry.

Flow Cytometry Analysis

The cells were trypsinized, centrifuged, resuspended in 400 μl of culture medium and filtered through a 50 μm mesh nylon filter. Then the cells were analyzed by a FACS-Calibur (Becton Dickinson) flow cytometer. For each sample 10000 events were collected. Fluorescein-fluorescence (for example green Fluorescent protein (GFP)) was measured through a 510-530 nm filter after excitation with an argon laser (200 mW) tuned on 488 nm. AlPcS$_{2a}$ was measured through a 670 nm longpass filter after excitation with a diode laser (50 mW) tuned on 635 nm. Cell doublets and dead cells were discriminated from single viable cells by gating. The data were analysed with CELLQuest Software (Becton Dickinson).

Example 1

Light-Induced Transfection as a Function of Light Dose

THX cells were treated with 20 μg/ml AlPcS$_{2a}$ for 18 hours, washed and incubated in sensitizer-free medium for 3 hours followed by 1 hour incubation with 5 μg pEGFP-N1/polylysine complex before light exposure for 1, 2, 3 or 4 minutes. Alternatively, after the AlPcS$_{2a}$ incubation the cells were washed and incubated for 4 hours in sensitizer-free medium before light treatment for 1, 2, 3 or 4 minutes followed by 1 hour with pEGFP-N1/polylysine complex as indicated on FIG. 1. GFP expression was analysed by flow cytometry 48 hours after light exposure. The charge ratio for pEGFP-N1/polylysine complex was 1.7.

Figure 1:
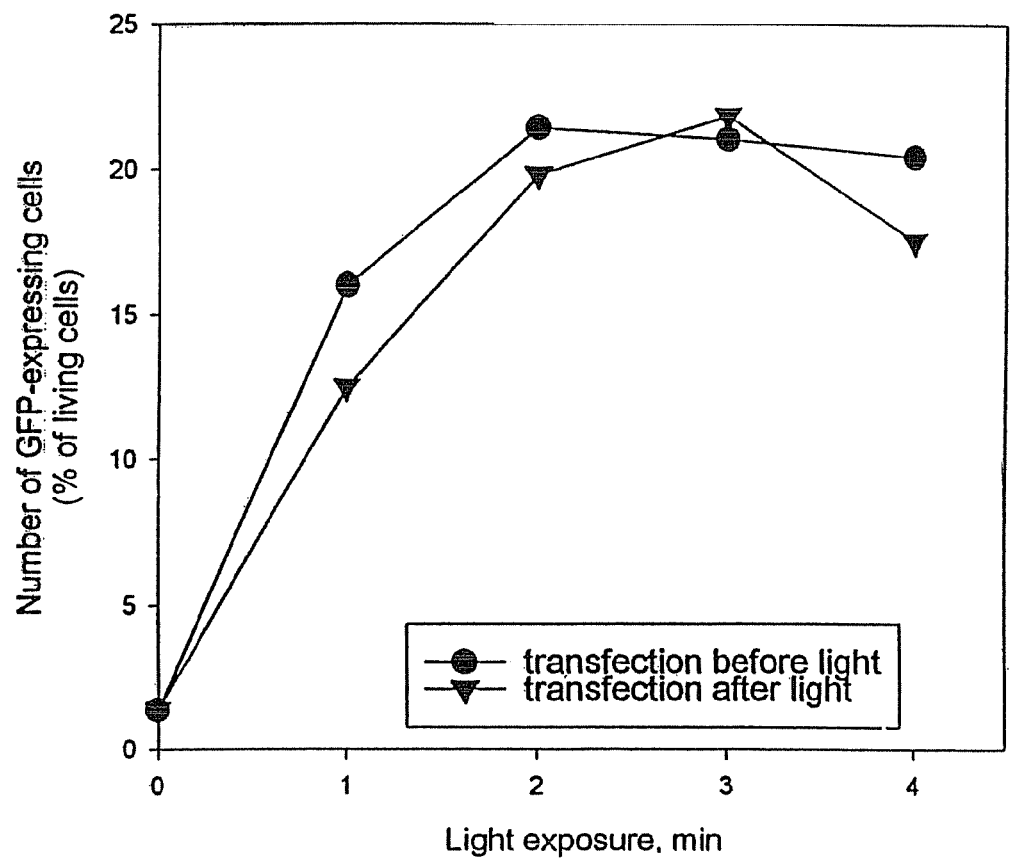
FIG. 1 shows light-induced transfection of THX cells with a pEGFP-N1 polylysine complex, wherein the cells are contacted with the pEGFP-N1 polylysine complex before or after the cells are exposed to light as indicated in the Figure.

The results are shown in FIG. 1 and it can be seen that the transfection of GFP is equally as effective when the plasmid-pLys complex (i.e. pEGFP-N1/pLys) is added to the cells after rather than before light exposure. It can also be seen that with both treatments the percentage of transfected cells depends on the length of time the cells are exposed to light with the percentage reaching a maximum level at around 2 minutes and then levelling off.

Example 2

Expression of GFP in HCT-116 Cells

HCT-116 cells were incubated with 20 μg/ml AlPcS$_{2a}$ for 18 hours followed by 4 hours in the absence of AlPcS$_{2a}$ before exposure to light. The cells were treated with pEGFP-N1/polylysine complex for 4 hours immediately before or after exposure to light as indicated on FIG. 2. The expression of GFP was measured by flow cytometry 2 days after the light exposure.

Figure 2:
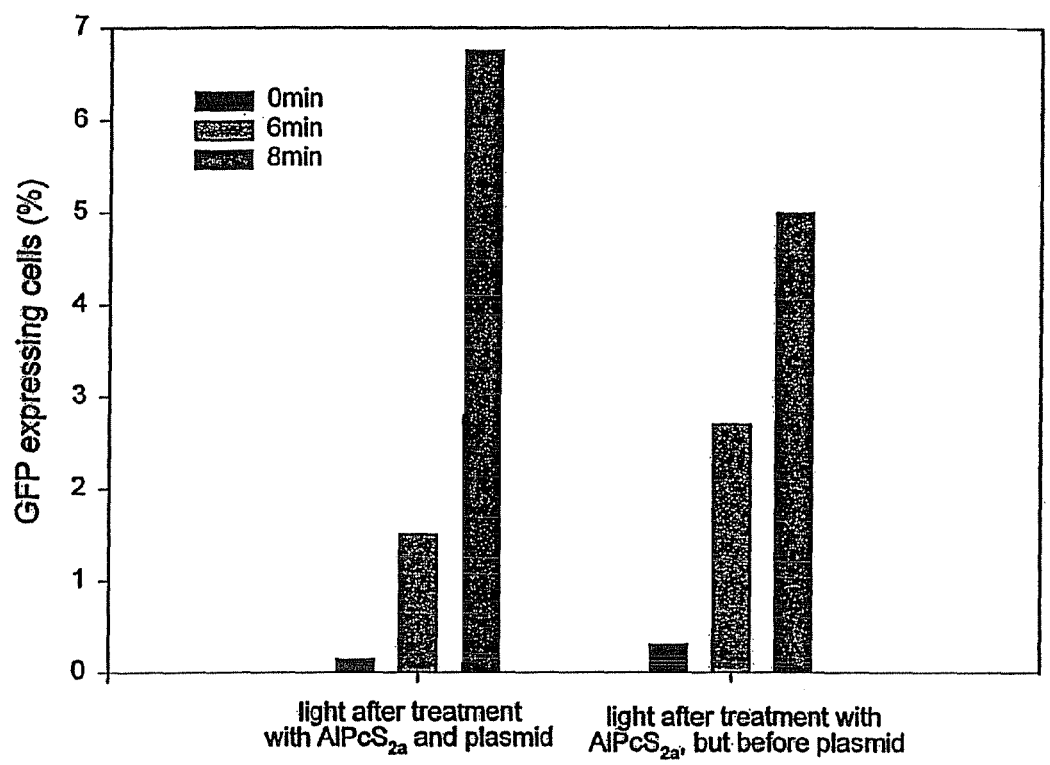
FIG. 2 shows light-induced transfection of HCT-116 cells with a pEGFP-N1 polylysine complex, wherein the cells are contacted with the pEGFP-N1 polylysine complex before or after the cells are exposed to light as indicated in the Figure.

The results are shown in FIG. 2 and it can be seen that, in a similar way to the transfection of the THX cells in Example 1, the transfection of GFP is equally as effective when the plasmid-plys complex (i.e. pEGFP-N1/pLys) is added to the cells after rather than before light exposure. Again, the percentage of transfected cells varies depending on the length of time the cells are exposed to light.

Example 3

Synergistic Effects of Adding Gelonin Before and After Photochemical Treatment

Gelonin is a plant toxin which efficiently inhibits protein synthesis when it is present in the cytosol of cells. THX cells were incubated with 20 μg/ml AlPcS$_{2a}$ for 18 hours followed by 4 hours in sensitizer-free medium before exposure to light. The cells were either co-treated with AlPcS$_{2a}$ and 1 μg/ml gelonin, or gelonin (1 μg/ml) was added to the medium immediately after light exposure for 18 hours after which it was removed from the medium as indicated on FIG. 3. Protein synthesis was measured 24 hours after light exposure.

Figure 3:
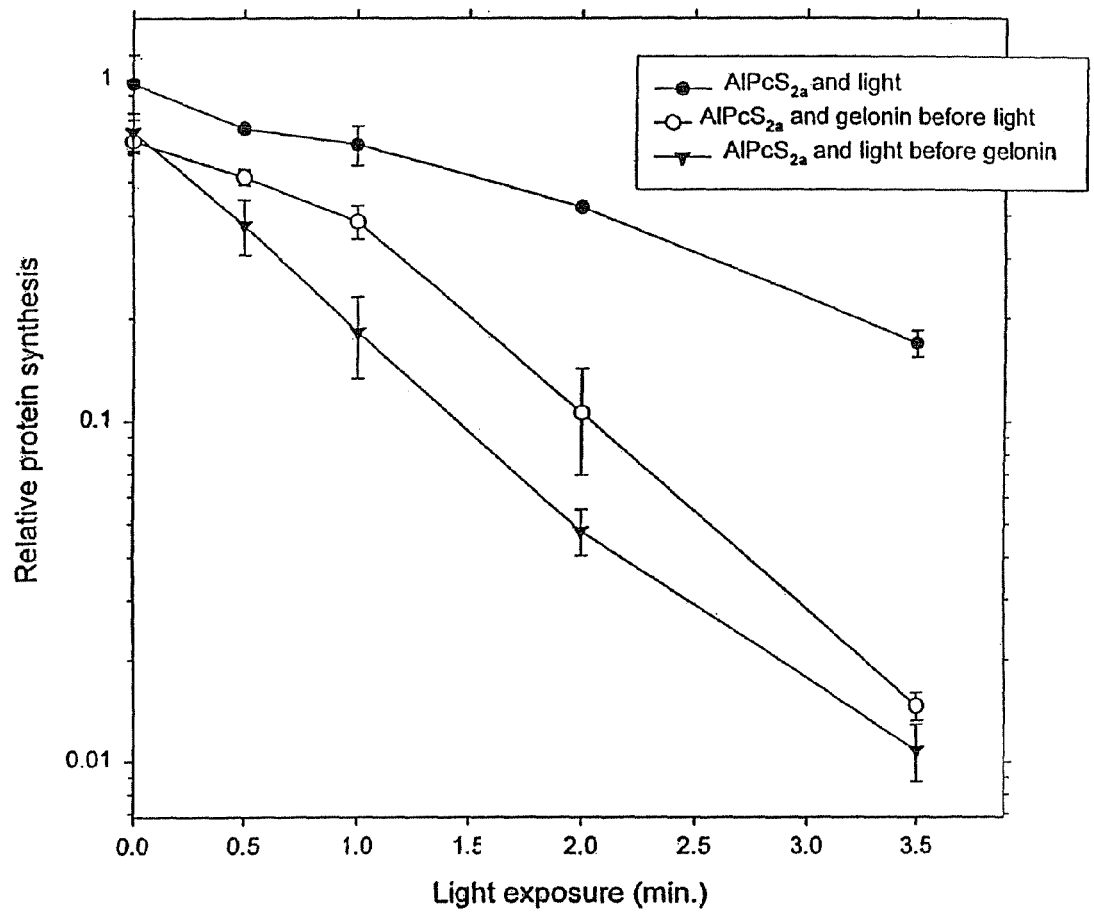
FIG. 3 shows light-induced treatment of THX cells with gelonin and thus a reduction in protein synthesis, wherein the cells are contacted with the gelonin molecule before or after the cells are exposed to light as indicated in the Figure.

The results are shown in FIG. 3 and it can be seen that although the photochemical treatment itself in the absence of gelonin leads to some reduction in protein synthesis, the presence of gelonin either before or after photochemical treatment induces a significantly greater inhibition of protein synthesis. This data shows that gelonin is internalised into the cells whether the gelonin is contacted with the cells before or after photochemical treatment.

Example 4

Effect of Chase Time on Light-Induced Transfection

THX cells were treated with 20 μg/ml AlPcS$_{2a}$ for 18 hours, washed and incubated in sensitizer-free medium for 4 hours before 3 minutes of light treatment. The cells were incubated in growth medium for the times indicated on FIG. 4 before treatment with pEGFP-N1/polylysine complex (charge ratio 1.7) for 1 hour. GFP expression was analysed by flow cytometry 48 hours after light exposure.

Figure 4:
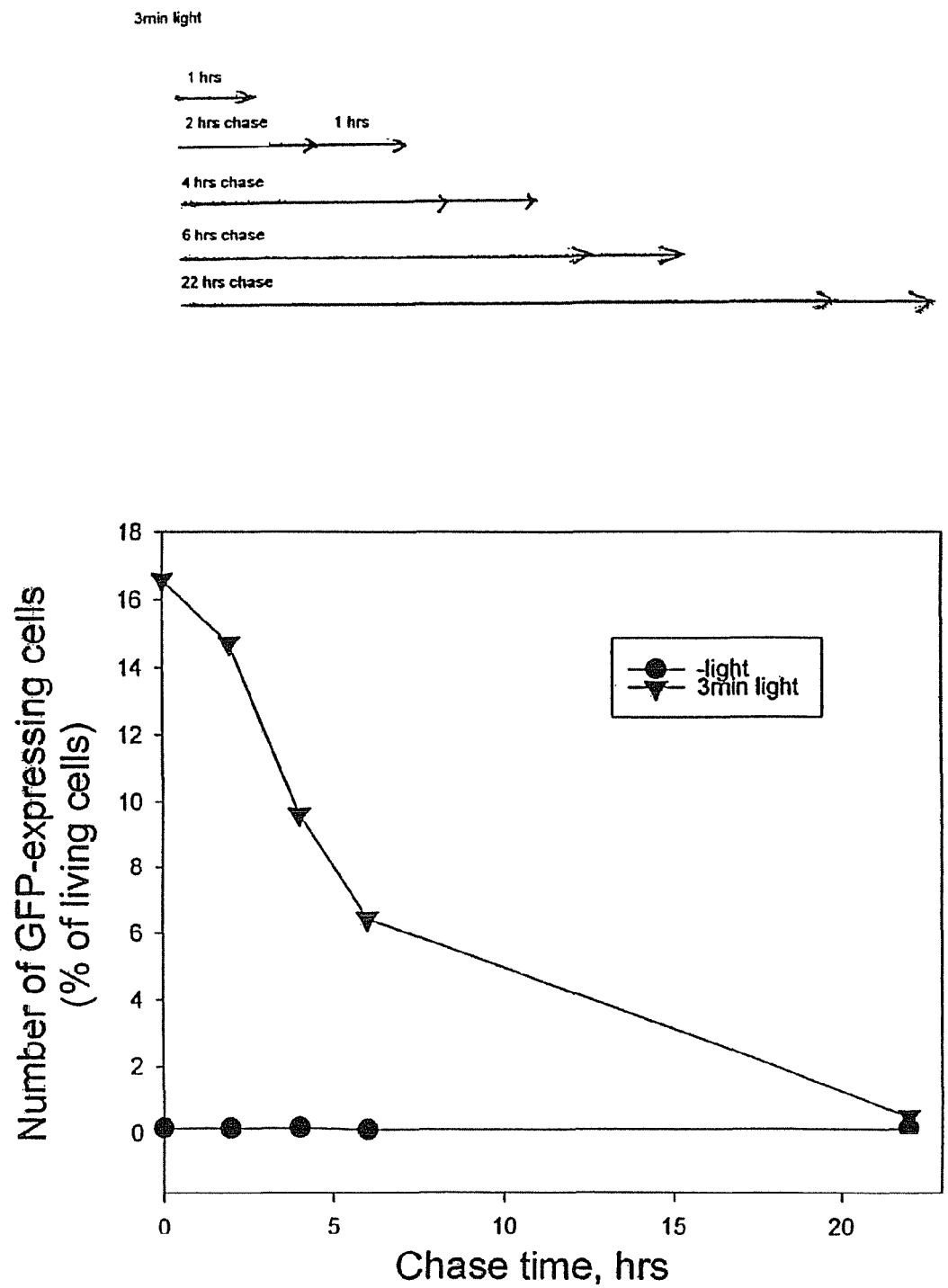
FIG. 4 shows the effect on the efficiency of light-induced transfection of THX cells of contacting the cells with the pEGFP-N1 polylysine complex immediately after light exposure and at later timepoints after light exposure.

The results are shown in FIG. 4 and it can be seen that for the best results the molecule to be internalised should be exposed to the cells relatively soon after the photochemical treatment, since the transfection with PEGFP-N1 declines with a half life of about 5 hours after light exposure.

Example 5

Efficiency of Transfection as a Function of a Transfection Pulse Relative to Illumination THX cells were treated with 20 μg/ml AlPcS$_{2a}$ for 18 hours, washed and incubated in sensitizer-free medium. Cells were given a pulse (0.5 or 1 hour, the width of the bar on FIG. 5 reflects the beginning and end of treatment) of treatment with the pEGFP-N1/polylysine complex either before (negative bascissa values) or after (positive abscissa values) 3 minutes of light exposure. GFP expression was analysed by flow cytometry 48 hours after light exposure. Data from several experiments have been normalized taking the efficiency of transfection when transfection is performed just before or just after light exposure as 100%.

Figure 5:
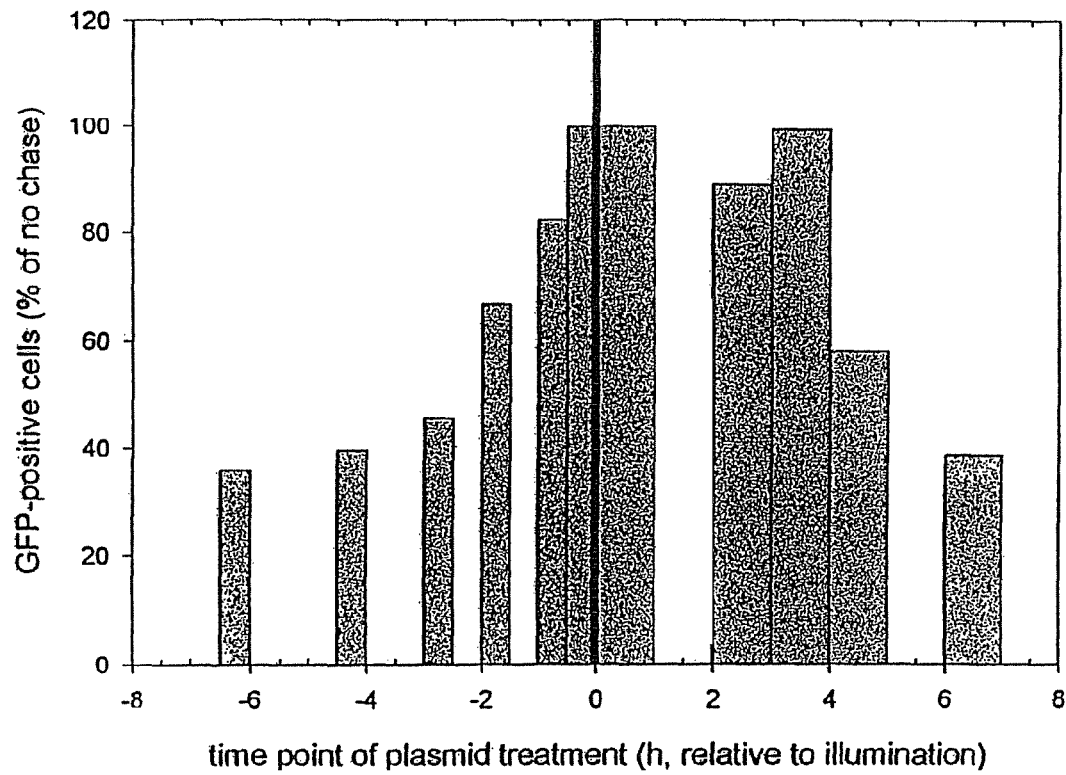
FIG. 5 shows the effect on the efficiency of light-induced transfection of THX cells when the cells are contacted with the pEGFP-N1 polylysine complex at varying timepoints before and after light exposure.

The results are shown in FIG. 5 and it can be seen that for the best transfection efficiency the cells should be exposed to the molecules to be internalised either shortly before or after exposure to light.

Example 6

Light-Induced Transfection—Dependence on Incubation Time with pEFGP-N1/Polylysine Complex THX cells were treated with 20 μg/ml AlPcS$_{2a}$ for 18 hours, washed and incubated in sensitizer-free medium for 4 hours before exposure to light, followed by incubation with pEGFP-N1/polylysine complex (charge ratio 1.7) for up to 6 hours as illustrated in FIG. 6A. GFP expression was analysed by flow cytometry 48 hours after light exposure. The number of GFP-expressing cells after such treatments are presented in FIG. 6B and the specificity of the different treatments presented in FIG. 6C.

Figure 6:
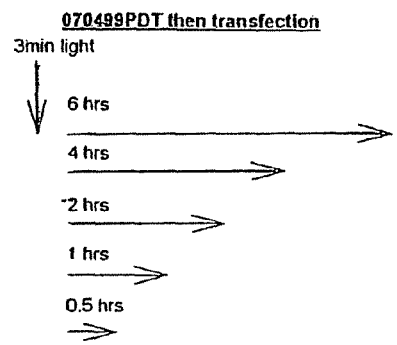
FIG. 6 shows the effect on light-induced transfection of THX cells when the cells are contacted with the pEGFP-N1 polylysine complex for various lengths of time after light exposure.
Figure 6:
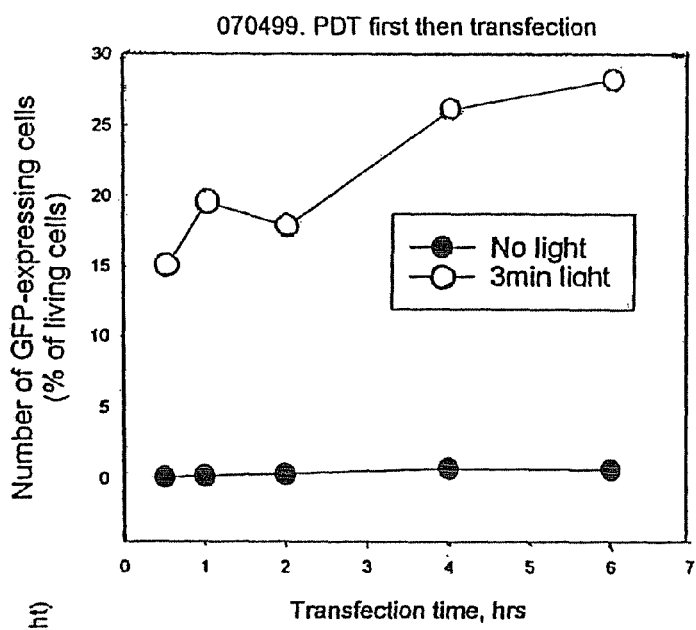
Figure 6:
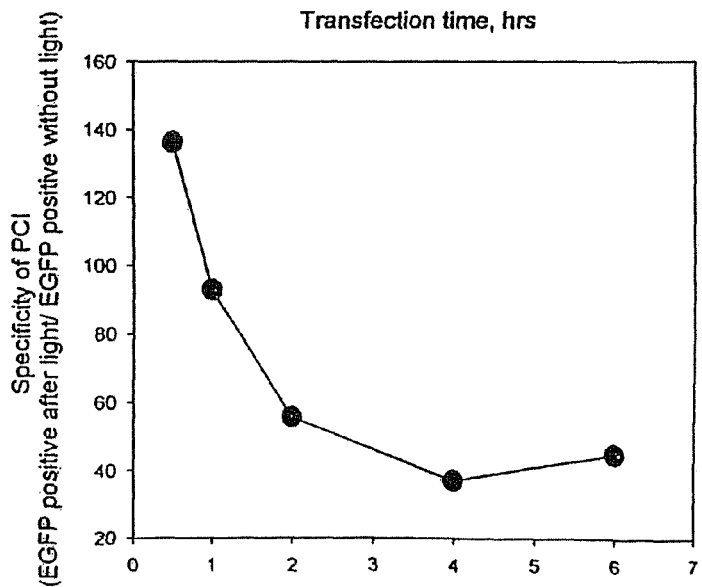
Figure 7:
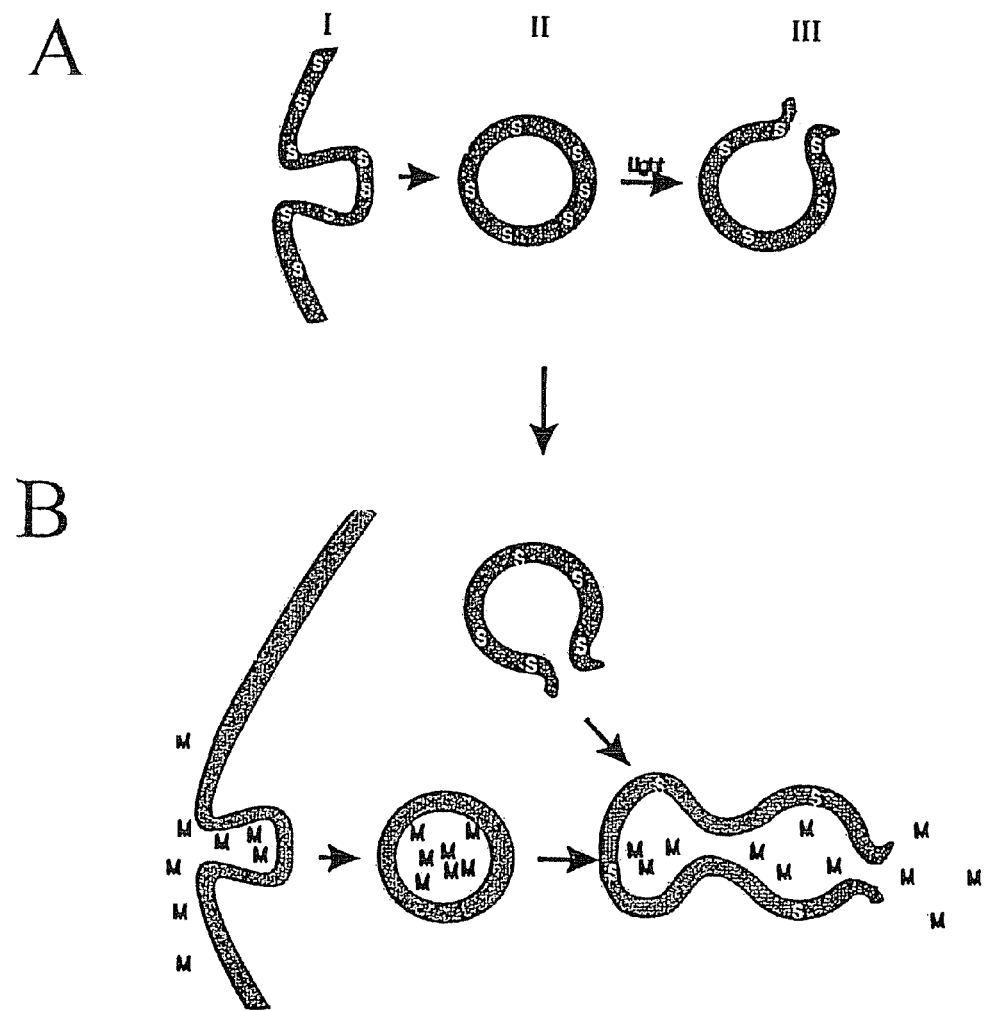
FIG. 7 shows a schematic representation of a potential model by which the current invention may work.

The results are shown in FIG. 6 and it can be seen that although the number of transfected cells increases with increasing incubation time with the pEGFP-N1/polylysine complex (FIG. 6B), the highest specificity of transfection occurs after the shortest incubation times (FIG. 6C).

Example 7

Treatment with pEGFP-N1/Polylysine Complex at 0° C.

This experiment was designed to test whether the photochemical treatment led to minor damage to the cell membranes, thereby meaning that the plasmid brought into contact with the cells after light treatment could leak through the plasma membrane.

THX cells were treated with 20 μg/ml AlPcS$_{2a}$ for 18 hours, washed and incubated in sensitizer-free medium for 4 hours before light exposure followed immediately afterwards by 45 minutes incubation at 0° C. with pEGFP-N1/polylysine complex (charge ratio 1.7). The cells were then either A) trypsinised and seeded out before being transferred to 37° C., or B) transferred to 37° C. without trypsinization. The cells were exposed to light as indicated on FIG. 8. GFP expression was analysed by flow cytometry 48 hours after light exposure.

After the incubation of the cells for 45 minutes at 0° C. with pEGFP-N1/polylysine complex the complex will stick to the cell surface but not be endocytosed. The THX cells were then either incubated in plasmid-free medium at 37° C. (FIG. 8B) or trypsinised (FIG. 8A) to remove the plasmid from the surface and seeded out in new dishes at 37° C. These experiments indicate that the plasmid/polylysine complex does not leak through the plasma membrane after photochemical treatment.

Example 8

Combination of 3-THPP and Light with Treatment with pEGFP-N1/Polylysine Complex

THX cells were treated with 0.25 μg/ml 3THPP for 18 hours, washed and incubated in sensitizer-free medium for 4 hours before light exposure, followed immediately afterwards by 1 hour incubation with pEGFP-N1/polylysine complex (charge ratio 1.7). The cells were exposed to light as indicated on FIG. 9 and analysed for GFP-expression flow cytometrically 48 hours after light exposure.

3-THPP is a photosensitizer the main location of which is not in endosomes or lysosomes. The results shown in FIG. 9 indicate that treatment of cells with 3-THPP before irradiation induces only a minor increase in GFP expression in comparison to the results shown in previous examples where the photosensitizing agent AlPcS$_{2a}$ is used. This indicates that a photosensitizing agent that is localised in endosomes and lysosomes may be advantageous.

Example 9

Combination of Photosensitizer and Light Pretreatment Allows Transfection of Cells Using Cationic Lipids HCT 116 cells were seeded out at a density of 75 000 cells/well in a 12-well plate one day before the experiment. The cells were incubated with the photosensitizer AlPcS$_{2a}$ (20 ug/ml) for 18 hours followed by a 7 h-chase in photosensitizer-free medium, and exposed to red light for 7 min. Then the cells were incubated with a DOTAP-complex (DOTAP was purchased from Boehringer) with the plasmid pEGFP-N1 (5:1 DOTAP/plasmid, 1 ug/ml pEGFP-N1) for 3 h, washed with the growth medium and incubated at 37° C. for 21 h before the expression of EGFP was measured by flow cytometry as described under Materials and Methods. Control cells were not exposed to light, otherwise the treatment was identical.

The results are shown in FIG. 10 and it can be seen that the PCI-treatment increases the transfection efficiency with the DOTAP/plasmid complex about 4 times.

Example 10

Effect of PCI on Adenovirus Transduction of THX Cells

Material

Fluorescein di-β-D-galactopyranoside (FDG) was purchased from Molecular Probes (F-1179). A 20 mM stock solution was prepared by dissolving the powder in a 1:1 mixture of DMSO/ethanol. The mixture was gradually added to an appropriate volume ice-cold water to make a 8:1:1 H$_2$0/DMSO/ethanol solution.

The recombinant virus AdCA17lacZ was formed and propagated in the human cell line 293, an Ad E1-transformed embryonic kidney cell line maintained in MEM F-11 medium supplemented with 10% FCS, 100 U/ml penicillin (Gibco-BRL), 0.1 mg/ml streptomycin (Gibco-BRL) and 2 mM glutamine.

Construction of Recombinant Virus

The recombinant adenovirus AdCA17lacZ encoding the *E. coli* lacZ gene under control of the human CMV promoter was obtained by homologous recombination using the pJM17 system in 293 cells (Addison et al., 1997, J. Gen. Virol., 78, 1653-1661). Recombinant vectors were plaque purified, grown to high titre in 293 cells and purified by cesium chloride banding as previously described (Hitt et al., 1995, Methods in Mol. Genetics., 7, 15-30).

Sensitizing of Cells

The THX cells (4×10$^5$ cells) were seeded out in 6 cm dishes and allowed to grow overnight. At approximately 60% confluence the growth medium was exchanged with 2 ml growth medium supplemented with 20 μg/ml AlPcS$_{2a}$, and the dishes were placed back into the incubator for 16-18 hours. The sensitizer-containing medium was then sucked off, and the cells were incubated in ordinary growth medium at least 4 hours before light treatment and virus infection.

Infection of Cells

Trypsin-EDTA was used to detach cells from three dishes and the mean cell number in the dishes was calculated by Bürcher chamber counting. Adenovirus dilutions were prepared in PBS with 0.68 mM CaCl$_2$ and 0.5 mM MgCl$_2$ according to the number of cells to infect. Usually the cells were infected at an m.o.i. (multiplicity of infection) of 1 and 10.

Before virus was added the cells were exposed to red light (Philips TL 20W/09, filtered through a Cinemoid 35 filter with a light intensity reaching the cells of 1.35 mW/cm$^2$) for 3 minutes. Subsequently the medium was sucked off and 200 μl virus suspension (or PBS with 0.68 mM CaCl$_2$ and 0.5 mM MgCl$_2$ in the cases of controls not treated with virus) was added to each dish. After incubation for 30 minutes at 37° C., 5 ml ordinary growth medium was added and the cells were allowed to grow for 48 hours.

β-Galactosidase Assay

The cells were detached by Trypsin-EDTA and resuspended in 5 ml growth media. After centrifugation for 5 minutes at 1000 rpm, the medium was sucked off, the cell pellets resuspended in 50 μl growth medium and the tubes placed in a 37° C. water bath for 5 minutes. Subsequently, 50 μl of 2 mM FDG-solution preheated to 37° C. was added and the tubes placed back into the water bath for 1 minute. Finally, 900 g growth medium was added and the tubes were incubated on ice for 30-60 minutes before the samples were analysed by flow cytometry as described above.

THX cells were treated with AlPCS$_{2a}$ (denoted as PS on FIG. 11) and adenovirus (denoted as "virus" on FIG. 11) and exposed to 3 or 4 minutes of light as described in Material and Methods and measured for β-galactosidase (β-gal) activity by flow cytometry. The total β-gal activity was quantified by integrating the β-gal positive cells and their β-gal activity. Both the number of β-gal positive cells and the mean β-gal activity was increased by the PCI treatment.

The results show that minimal infection of THX cells occurs when the cells are incubated with virus alone or virus and photosensitising agent but that photochemical treatment, i.e. the addition of light to the photosensitising agent significantly potentiates the transduction of cells (as shown by the increase in β-gal activity).

Example 11

Effect of Photochemical Treatment on the Intracellular Localisation of an Endocytosis Marker Molecule THX cells were seeded out into Falcon 3001 dishes (2.5× 10$^4$ cells per dish) and the next day treated with 20 μg/ml AlPcS$_{2a}$ for 18 h, washed from AlPcS$_{2a}$ and incubated in AlPcS$_{2a}$-free medium for 4 h. Then the cells were exposed to light for 4 min before a 3 h incubation with 5 mg/ml of the endocytic marker FITC-dextran. Non-illuminated cells were treated in a similar way except for illumination. The intracellular localisation of FITC-dextran in unfixed cells was observed with a Zeiss Axioplan fluorescence microscope (Oberkochen, Germany) using an objective with 63× magnification, a 450-490 nm band pass excitation filter and a 510-540 band pass emission filter. Fluorescence micrographs were recorded by means of a cooled charge-coupled device (CCD) camera (Photometrics Inc., Tucson, Ariz.).

The results show (FIG. 12) that PCI with light given before the fluorescent endocytic marker FITC-dextran shifts the localisation of this marker from endocytic vesicles (the spots seen in panel A for non-illuminated cells) to the cytosol (the diffuse fluorescence seen in panel B for illuminated cells). Thus when the light treatment is given before the macromolecule to be internalised the macromolecule is very rapidly translocated to the cytosol, substantially decreasing the possibilities for lysosomal degradation of the macromolecule.

Example 12

Effects of Photochemical Treatments on Gelonin Toxicity in THX- and HCT 116 Cells Gelonin is a plant toxin that efficiently inhibits protein synthesis when it is present in the cell cytosol, but which is not able to reach the cytosol on its own, and therefore is quite non-toxic to intact cells. For the treatment with gelonin 25×10$^3$ cells per well were seeded out into 24-well plates (Nunc, Denmark). The next day 20 μg/ml AlPcS$_{2a}$ was added, and the cells were incubated for 18 h at 37° C. All the procedures after AlPcS$_{2a}$ addition were carried out in subdued light. For the "light before" strategy, the cells were washed from AlPcS$_{2a}$ and incubated in AlPcS$_{2a}$-free medium for 4 h. Then the cells were exposed to light (as indicated in the figures) before the treatment with 1 μg/ml gelonin for 18 h. For the "light after" strategy the cells were co-incubated with 20 μg/ml AlPcS$_{2a}$ and 1 μg/ml gelonin for 18 h, and washed before exposure to light as indicated in the figure.

Non-illuminated cells were treated in a similar way except for illumination. The treated cells were washed once with culture medium and after addition of fresh medium incubated at 37° C. before further analysis. Inhibition of protein synthesis was assayed by [$^3$H]-leucine incorporation into protein 24 h after light exposure. Illumination was performed from a bench with four light tubes (Philips TL 20W/09) and a long pass filter with a cut off at 550-600 nm. The light intensity reaching the cells was 13.5 W/m$^2$.

The example shows that in both THX- (FIG. 13A) and HCT 116 (FIG. 13B) cells the "light before" strategy works better than the "light after" method. Thus, for THX-cells at the highest light dose the inhibition of protein synthesis was about 3-fold more potent with "light before" than with "light after". It can also be seen that in both cell lines gelonin in itself had no toxic effect without the PCI treatment, showing the potency and specificity in the induction of the toxin effects that can be achieved by the photochemical treatment.

Example 13

Photochemical Stimulation of Adenovirus-Mediated Gene Transduction

5×10$^4$ THX cells per well were seeded out into 6-well plates. The next day 20 μg/ml AlPcS$_{2a}$ was added, and the cells were incubated for 18 h at 37° C. All the procedures after AlPcS$_{2a}$ addition were carried on in subdued light. For the "light before" strategy, the cells were washed from AlPcS$_{2a}$ and incubated in AlPcS$_{2a}$-free medium for 4 h. Then the cells were exposed to light for 3 min before the treatment with the adenoviral vector AdHCMV-lacZ (also referred to in Example 10 as AdCA17lacZ) at a multiplicity of infection (MOI) of 1 for 30 min. This vector contains a β-galactosidase reporter gene whose expression can be analysed by flow cytometry (see below).

For the "light after" strategy AlPcS$_{2a}$-treated and washed cells were first treated with adenovirus at the same concentration and for the same time as indicated above, washed, and after addition of fresh culture medium exposed to light. Non-illuminated cells were treated in a similar way except for illumination.

The treated cells were washed once with culture medium and after addition of fresh medium incubated at 37° C. before further analysis. β-galactosidase expression was analysed by flow cytometry two days after light exposure. Detailed methods for construction of the virus (which is referred to either as AdHCMV-lacZ or AdCA17lacZ), treatment of the cells, illumination and analysis of β-galactosidase expression are described under Example 10.

The results (FIG. 14) show that the photochemical treatment using the "light before" procedure (shown by the bars on the right hand side of FIG. 14) increases the percentage of β-galactosidase-expressing cells about 6-fold; from 2.5% to 15% under these experimental conditions. It can also be seen that the effect with the "light before" procedure was almost equal to what was obtained with the "light after" method (shown by the bars on the left hand side of FIG. 14).

Example 14

Effect of the Incubation Time on the Efficiency of Light-Induced Transfection $5 \times 10^4$ THX cells or $7.5 \times 10^4$ HCT 116 cells per well were seeded out into 6-well and 12-well plates, respectively. The next day 20 µg/ml $AlPcS_{2a}$ was added, and the cells were incubated for 18 h at 37° C. All the procedures after $AlPcS_{2a}$ addition were carried on in subdued light. The cells were washed from $AlPcS_{2a}$ and incubated in $AlPcS_{2a}$-free medium for 4 h. Then the cells were exposed to light (3 min for THX cells or 7 min for HCT 116 cells) before treatment with pEGFP-N1/polylysine (5 µg/ml pEGFP-N1) complex for the times indicated on FIG. 15. Non-illuminated cells were treated in a similar way except for illumination. The treated cells were washed once with culture medium and after addition of fresh medium incubated at 37° C. for 2 days before analysis of EGFP expression by flow cytometry (see Materials and Methods). Illumination was performed from a bench with four light tubes (Philips TL 20W/09) and a long pass filter with a cut off at 550-600 nm. The light intensity reaching the cells was 13.5 W/m². pEGFP-N1/polylysine complex (charge ratio 1.7) was prepared by gently mixing plasmid and polylysine solutions prepared separately: 5 µg pEGFP-N1 plasmid was diluted in 75 µl water and 5.3 µg polylysine diluted in 75 µl water. The solutions were mixed and incubated for 30 min at room temperature, diluted with culture medium to 1 ml and added to the cells.

The results (FIG. 15) show that both in THX and in HCT 116 cells transfection by DNA/polylysine complexes can be strongly induced by the "light before" photochemical treatment. It can be seen that the stimulation of transfection is effective already after short incubations times with DNA, at least down to 30 min incubation time. The light-induced transfection increases with the incubation time, however, seemingly levelling off after about 2 h incubation with DNA.

Example 15

Effect of the Light First PCI Strategy on Transfection of THX Cells Mediated by Poly-L-Lysine Using $TPPS_{2a}$ as the Photosensitiser Tetraphenylporphine disulfonate ($TPPS_{2a}$), lot #04197, was produced by Porphyrin Products (UT, USA). $TPPS_{2a}$ was dissolved in DMSO.

The plasmid pEGFP-N1 was purchased from Clontech Laboratories Inc. (CA, USA; cat. no. 6085-1). The batch used (lot# EGFP-N1-1002) was produced by ELIM Biopharmaceuticals, Inc. (CA, USA) and delivered at a concentration of 5 mg/ml in sterile water. A stock solution of 0.5 mg/ml was made up in sterile TE-buffer pH 7.4 (1 mM Tris-HCl, 1 mM EDTA) and kept at −20° C.

The THX human melanoma cells were cultivated in RPMI 1640 medium supplemented with 10% FCS (fetal calf serum), Penicillin/Streptomycin and L-glutamine. In subdued light, the medium was removed and medium containing 2 µg/ml $TPPS_{2a}$ was added. The cells (protected from light) were incubated at 37° C. for 18 h. The cells were washed three times with medium and for the PLL-L ("light after") samples 1 ml medium containing a pEGFP-N1/Poly-L-Lysine complex was added. The complex contained 5 µg pEGFP-N1 and had a charge ratio of poly-L-lysine (PLL) to DNA of 1.7. After 4 h of further incubation at 37° C. in the dark the medium was removed, and the cells were washed once with medium. 1 ml medium was added and the cells were exposed to blue light as indicated in FIG. 16 and described under Materials and Methods. For the L-PLL ("light before") samples the first 4 h incubation was in medium without pEGFP-N1/PLL complex, the complex being added immediately after illumination and removed after a further 4 h incubation. The cells were incubated for 2 days (still protected from light) prior to analysis for EGFP expression by flow cytometry. For this analysis the cells were trypsinized (Trypsin-EDTA, Sigma, Mo., USA), resuspended in 400 µl RPMI medium and filtered through a 50 µm mesh nylon filter before analysis in a FACSCalibur flow cytometer (Becton Dickinson, Calif., USA). EGFP was measured through a 510-540 nm filter after excitation at 488 nm. Propidum iodide (1 µg/ml) was used to discriminate dead cells from viable cells, and pulse-processing was performed to discriminate cell doublets from single cells. 10 000 events were collected for each sample, and the data were analysed with CELLQuest Software (Becton Dickinson, Calif., USA).

Results

As can be seen in FIG. 16 for poly-L-lysine mediated transfection of THX cells the "light before" addition of the transfer molecule approach works as well as the "light after" approach when using the $TPPS_{2a}$ photosensitiser.

Example 16

Effect of the Light First PCI Strategy on Transfection of THX Cells Mediated by Poly-L-Lysine Using $TPPS_4$ as the Photosensitiser THX cells were grown and treated as described under Example 15, except that the $TPPS_4$ photosensitizer (75 µg/ml) was used instead of $TPPS_{2a}$.

Results

From FIG. 17 it is apparent that for poly-L-lysine mediated transfection of THX-cells the "light before" approach works slightly better than the "light after" approach when using the $TPPS_4$ photosensitiser, but both methods still achieved transfection.

Example 17

Effect of the Light First PCI Strategy on Transfection of HCT 116 Cells Mediated by Poly-L-Lysine, Using $TPPS_{2a}$ as the Photosensitiser HCT 116 cells were grown and treated as described under Example 15.

Results

From FIG. 18 it can be seen that for poly-L-lysine mediated transfection of HCT 116 cells the "light before" approach works as well as the "light after" approach when using the $TPPS_{2a}$ photosensitiser.

Example 18

Effect of the Light First PCI Strategy on Transfection of HCT 116 Cells Mediated by Poly-L-Lysine, Using $TPPS_4$ as the Photosensitiser THX cells were grown and treated as described under Example 15, except that the $TPPS_4$ photosensitizer (75 µg/ml) was used instead of $TPPS_{2a}$.

Results

FIG. 19 shows that for poly-L-lysine mediated transfection of THX cells the "light before" approach works as well as the "light after" approach when using the TPPS$_4$ photosensitiser.

Example 19

Effect of the Light First PCI Strategy on Transfection Mediated by DOTAP Using TPPS$_4$ as the Photosensitiser HCT 116 cells were cultivated in RPMI 1640 medium supplemented with 10% FCS (fetal calf serum), Penicillin/Streptomycin and L-glutamine. In subdued light, the medium was removed and medium containing 75 µg/ml TPPS$_4$ was added. The cells (protected from light) were incubated at 37° C. for 18 h. The cells were washed three times with medium and for the DOTAP-L ("light after") samples 1 ml medium containing a complex of 1 µg pEGFP-N1 and 5 µg DOTAP was added. After 4 h of further incubation at 37° C. in the dark the medium was removed, and the cells were washed once with medium. 1 ml medium was added and the cells were exposed to blue light as indicated in FIG. 20 and described under "Materials and Methods". For the L-DOTAP ("light before") samples the first 4 h incubation was in medium without pEGFP-N1/DOTAP complex, the complex being added immediately after illumination and removed after a further 4 h incubation. The cells were incubated for 1 day (still protected from light) prior to analysis for EGFP expression by flow cytometry as described under Example 15.

Results

From FIG. 20 it can be observed that for transfection of HCT 116 cells mediated by the cationic lipid DOTAP the "light before" approach works substantially better than the "light after" approach when using the TPPS$_4$ photosensitiser. The "light before" approach seems to be especially advantageous for transfection mediated by cationic lipids.

Example 20

Effect of the Light First PCI Strategy on Transfection Mediated by SuperFect® Using TPPS$_{2a}$ as the Photosensitiser SuperFect® was purchased from QIAGEN AG.
Preparation of plasmid/Superfect® complexes
Plasmid/SuperFect® complexes were prepared as follows: (i) pEGFP-N1 was diluted with RPMI 1640 medium (without serum, proteins and antibiotics). (ii) SuperFect® (2 µl per µg DNA) was added to the plasmid solution and the contents were mixed by vortexing for 10 s. (iii) The solution was incubated for 10-20 min at room temperature to allow complex formation. (iv) 400 µl of cell growth medium (with serum and antibiotics) was added to the tubes containing the transfection complexes and the contents were mixed by pipetting up and down two times, and the total volume was immediately transferred to the cells.

Treatment of the Cells

HCT 116 cells (75000 cells/well, 1 ml/well) were seeded into 12-well plates (Costar Corning, N.Y., USA) and allowed to attach for six hours. 1 ml medium with 0.7 µg/ml TPPS$_{2a}$ was added, and the cells were incubated for 18 h (5% v/v CO$_2$, 37° C.). The cells were washed three times with medium and incubated for 4 h (37° C., 5% v/v CO$_2$) in serum-containing medium. The cells were illuminated by exposure to a bank of four fluorescent tubes (Osram 18W/67) with the highest fluence around 420 nm. The plasmid/SuperFect® complexes were added immediately after the light exposure, and the cells were incubated with the complexes for 1 or 4 h. The cells were then washed 4 times in RPMI medium, and after addition of 1 ml medium they were incubated further for two days. Then the expression of EGFP was analysed by flow cytometry as described under Example 15.

Results

It can be seen (FIG. 21) that PCI substantially improves SuperFect® transfection under all conditions tested. E.g. for 0.75 µg DNA and 1 h transfection time a 9-fold improvement was seen, while for 0.75 µg DNA and 4 h transfection time a 10-fold enhancement was observed.

Example 21

Effect of the Light First PCI Strategy on Adenovirus Mediated Gene Transduction of HCT 116 Cells Using TPPS$_{2a}$ as the Photosensitiser HCT 116 cells were cultivated in RPMI 1640 medium supplemented with 10% FCS (fetal calf serum), Penicillin/Streptomycin and L-glutamine. In subdued light, the medium was removed and medium containing 1 µg/ml TPPS$_{2a}$ was added to each well. The cells (protected from light) were incubated at 37° C. for 18 h. The cells were washed three times with medium. The cells were then infected with the Ad-HCMV-LacZ adenovirus at different time points before or after illumination (which was always 4 h after the removal of the photosensitizer). The cells were incubated further for 2 days (still protected from light) prior to analysis for β-galactosidase activity by flow cytometry as described under Example 10 (Materials and Methods).

Results

FIG. 22 shows the effect of the timing of the light treatment relative to the delivery of the virus on the PCI effect on adenovirus mediated gene transduction. It can be seen that for the "light before" approach (the right side of the Y-axis) the PCI illumination is effective for at least 13 h, so that the virus can be administered up to at least 13 h after illumination, still maintaining the positive PCI effects on transduction. This is very important from a clinical point of view because it allows the clinician great flexibility in designing the treatment and coordinating it to other treatments the patient might receive, e.g. to surgical procedures.

Example 22

Effect of the Light First PCI Strategy on Transfection of HCT 116 Cells Mediated by Poly-D-Lysine Using AlPcS$_{2a}$ as the Photosensitiser HCT 116 cells were grown, treated and analysed as described under Example 15 except that poly-D-lysine was used instead of poly-L-lysine in making the complex with pEGFP-N1.

Results

From FIG. 23 it can be observed that PCI with the "light before" protocol works well also when the polycation poly-D-lysine is used as the transfection agent.

Example 23

Effect of the Light First PCI Strategy on Cell Killing by the Cytostatic Agent Bleomycin Using TPPS$_{2a}$ as the Photosensitiser Tetraphenylporphine disulfonate (TPPS$_{2a}$), lot #04197, was produced by Porphyrin Products (UT, USA). TPPS$_{2a}$ was dissolved in DMSO.

The Chinese hamster lung fibroblast cell line V-79 was used in this study.

MTT (3-[4,5-Dimethylthiazol-2-yl]-2,5-diphenyltetrazolium bromide) was from Sigma (MO, USA; cat. no. M 2128), dissolved in PBS to a concentration of 5 mg/ml, sterile filtered and stored at 4° C.

Bleomycin (ASTA Medica) 15 000 IE/KY was obtained from the pharmacy at the Norwegian Radium Hospital. 1 IE corresponds to 1 mg of Bleomycin. The bleomycin powder was dissolved in sterile 0.9% NaCl-solution to a final concentration of 2 mM.

Cell Cultivation

The V-79 cells were cultured in RPMI 1640 medium (Gibco) supplemented with 10% fetal calf serum, 100 U/ml penicillin, 100 µg/ml streptomycin and 2 mM glutamine (all Gibco BRL, Paisley, Scotland) at 37° C. and 5% $CO_2$ in a humid environment.

Treatment of the Cells

The cells (75 000 cells/well, 1 ml/well) were seeded into 12-well plates (Costar Corning, N.Y., USA) and allowed to attach for 6 h. To some of the wells 1 ml medium with 0.7 µg/ml $TPPS_{2a}$ was added (see Table 1), and the cells were incubated for 18 h (5% v/v $CO_2$, 37° C.) The cells were washed three times with medium. The cells were then incubated in serum-containing medium for 4 h. The medium was removed, new medium was added and the cells were illuminated by exposure to light from a box containing a bank of four fluorescent tubes (Osram 18W/67) with the highest fluence around 420 nm.

Different doses of bleomycin were immediately added. After 1 or 4 h incubation with bleomycin the cells were washed once with RPMI-medium, 1 ml of medium was added and after 3 days of incubation cell survival was measured by the MTT assay. This method is based on reduction of a water-soluble tetrazolium salt (MTT) to a purple, insoluble formazan product by mitochondrial dehydrogenases present in living, metabolically active cells. One ml medium containing 0.25 µg MTT is added to the cells, followed by 4 h incubation (37° C., 5% v/v $CO_2$). The resulting formazan crystals are dissolved by adding 200 µl isopropanol (Sigma, Mo., USA) per well. The solution is transferred to a 96 wells plate which is read by a Multiskan EX microplate reader (Labsystems, Finland) with a 570 nm bandpass filter. Cell survival is calculated as percent of control cells not receiving light treatment.

Results

FIG. 24 shows that PCI with the "light before", approach can also increase the biological effect of a low molecular weight, clinically approved chemotherapeutic agent (bleomycin). Thus, it can be seen that for the 100 µM bleomycin dose a substantial light-induced increase in the cytotoxicity of bleomycin can be observed (■ and ● in FIG. 24). The lack of effect at the lowest dose of bleomycin (♦ in FIG. 24) shows that this increased cytotoxicity is not a result of the photochemical treatment per se, since this sample series received the same photochemical treatment as the 100 µM bleomycin series without observable light-induced effects on cell survival.

Example 24

PCI with Gelonin for Treatment of Tumours in a Mouse In Vivo Model

Animals

Balb/c (nu/nu) nude female mice were bred at the Animal Department of the Institute for Cancer Research. The mice were kept under specific pathogen-free conditions.

Water and food was given ad libitum. All procedures involving mice were carried out in agreement with the protocols approved by the animal care committee at the Norwegian Radium Hospital, under control by the National Ethical Committee's guidelines on animal welfare. The mice were on average 20-25 g (5-8 weeks old) at the start of the experiments, and we used at least 5 mice per experiment group. The WiDr human adenocarcinoma used in the present study, was propagated by serial transplantation into the Balb/c (nu/nu) mice. The tumours were minced to homogeneity by a scalpel and 20 µl of the solution injected subcutaneously on the right hip of each mouse. The tumour size was measured two or three times per week by measuring two perpendicular diameters. Tumour volume was calculated using the following formula:

$$V=(W^2 \times L)/2$$

where W is the width and L the length diameters of the tumours measured.

Treatment

The mice were randomly allocated to the different groups shown in Table 1 and FIG. 25. A stock solution of $AlPcS_{2a}$ was diluted to 1.25 mg/ml in PBS and injected intraperitoneally to a final concentration of 10 mg/kg when the tumours had reached a volume of approximately 100 $mm^3$. 48 h after the injection of $AlPcS_{2a}$ the tumours were exposed for 16 min to red light (see below). Immediately after light exposure gelonin (50 µg total amount in a 2 mg/ml solution, i.e. 25 µl) was injected intratumorally. The mice were kept in the dark for 1 week after the injection of $AlPcS_{2a}$.

Light Treatment

The tumours were illuminated with a 150 W halogen lamp (Xenophot HLX64640) filtered with a 580 nm long pass and a 700 nm short pass filter emitting 150 $mW/cm^2$. The animals were covered with aluminium foil except above the tumour area where a hole in the foil with a diameter 2 mm larger than the tumour diameter had been made. The tumours were exposed to 145 $J/cm^2$ of light. Tumour volumes were measured two or three times per week as described above. Mice were killed when the tumours reach a diameter of approximately 20 mm. The fraction of tumour-free mice 30 days after illumination was scored (Table 1), and the mean tumour volume in each treatment group was recorded (FIG. 25).

Results

TABLE 1

The mice were treated as described above and the occurrence of tumours was recorded 30 days after illumination.

| GROUP No. | TREATMENT | FRACTION TUMOUR-FREE MICE 30 DAYS AFTER ILLUMINATION | % TUMOUR-FREE MICE 30 DAYS AFTER ILLUMINATION |
|---|---|---|---|
| 1 | Untreated | 1/8 | 13 |
| 2 | PBS + light | 0/7 | 0 |
| 3 | Gelonin | 0/8 | 0 |
| 4 | Gelonin + "light before" | 0/5 | 0 |
| 5 | $AlPcS_{2a}$ | 0/10 | 0 |
| 6 | $AlPcS_{2a}$ + gelonin | 0/7 | 0 |
| 7 | $AlPcS_{2a}$ + light | 2/11 | 18 |
| 8 | $AlPcS_{2a}$ + gelonin + "light before" | 4/5 | 80 |

From Table 1 it can be seen that PCI with gelonin using the "light before" approach (group 8) cured 80% (4 of 5) mice from their tumours. In contrast gelonin alone showed no effect, neither with (group 4) nor without (group 3) additional light treatment (without AlPCS$_{2a}$). Neither did gelonin in combination with AlPcS$_{2a}$ without light treatment (group 6) show any effect. A low cure rate was seen in untreated animals (group 1) probably due to a spontaneously disappearing tumour. A low cure rate could also be observed for animals receiving AlPcS$_{2a}$ and light treatment (group 7), due to a photodynamic therapy (PDT) effect that was independent on the presence of gelonin. However, this PDT effect (18% cure) was significant lower than what was found for the PCI treatment with gelonin (801, group 8). Since gelonin on its own had no effect whatsoever the high cure rate in the PCI group cannot be explained by an additive effect of PDT and gelonin, but must be due to a synergistic effect where the PCI treatment realizes the toxic potential of gelonin.

FIG. 25 shows the effect of the PCI treatment on the mean tumour volume in some of the treatment groups. It can be seen that in the group receiving only gelonin (Δ) the tumours grew as fast as in animals given a placebo treatment of phosphate buffered saline (PBS) injection combined with illumination (■). In animals receiving only the photochemical treatment, but no gelonin (◇) the tumour growth was delayed, but the tumours started growing again approximately 15 days after illumination.

In contrast, for the animals receiving the full gelonin PCI treatment (●) no increase in the mean tumour volume could be observed even 33 days after illumination.

The invention claimed is:

1. A method for introducing a molecule into the cytosol of a cell, said method comprising
    contacting said cell with a photosensitising agent,
    contacting said cell with an isolated transfer molecule wherein said transfer molecule consists of a protein, peptide, or antibody or fragment thereof, and
    irradiating said cell with light of a wavelength effective to activate the photosensitising agent,
    wherein said transfer molecule is taken up into endosomes by the cell and wherein as a consequence of said irradiation said transfer molecule is released into the cytosol of said cell,
    wherein said irradiation is performed prior to cellular uptake of said transfer molecule into any intracellular compartment, and
    wherein one or both of the photosensitising agent and the transfer molecule is attached to, associated with, or conjugated to, one or more carrier molecules, targeting molecules or vectors.

2. A method for introducing a molecule into the cytosol of a cell, said method comprising
    contacting said cell with a photosensitising agent,
    irradiating said cell with light of a wavelength effective to activate the photosensitising agent and, at the same time or at a time after the irradiation,
    contacting said cell with an isolated transfer molecule wherein said transfer molecule consists of a protein, peptide, or antibody or fragment thereof,
    wherein said transfer molecule is taken up into endosomes by the cell and wherein as a consequence of said irradiation said transfer molecule is released into the cytosol of said cell, and
    wherein one or both of the photosensitising agent and the transfer molecule is attached to, associated with, or conjugated to, one or more carrier molecules, targeting molecules or vectors.

3. A method as claimed in claim 1 wherein the cell is contacted with the transfer molecule at a time point after irradiation has taken place.

4. A method as claimed in claim 1 wherein the cell is contacted with said transfer molecule 0 to 4 hours after irradiation has taken place.

5. A method as claimed in claim 1 wherein the cell is contacted with the transfer molecule at the same time as the irradiation.

6. A method as claimed in claim 1 wherein the transfer molecule is contacted with said cell for 30 minutes to 6 hours.

7. A method as claimed in claim 1 wherein said method is performed on cells in vitro or in vivo.

8. A method as claimed in claim 1 wherein said transfer molecule, or a part or fragment thereof, is presented or expressed on the cell surface.

9. A method as claimed in claim 8 wherein said cell is an antigen-presenting cell.

10. A method as claimed in claim 1 wherein said transfer molecule is a cytotoxic drug.

11. A method as claimed in claim 1 wherein the photosensitising agent is selected from the group consisting of tetrakis (4-sulfonatophenyl)porphyrin, tetraphenylporphyrin disulfonate, aluminium phthalocyanine disulfonate and other amphiphilic photosensitizers.

12. A method as claimed in claim 1 wherein said photosensitizing agent is a compound being 5-aminolevulinic acid or an ester of 5-aminolevulinic acid or a pharmaceutically acceptable salt thereof.

13. A method as claimed in claim 1 wherein said photosensitizing agent is contacted with said cells for 4 to 24 hours prior to irradiation, preferably for that period immediately prior to irradiation.

14. A method as claimed in claim 1 wherein said photosensitizing agent is removed after contact with said cell for 1 to 4 hours prior to irradiation.

15. A method as claimed in claim 1 wherein the carrier, targeting molecule or vector to which or with which, the transfer molecule is attached, associated, or conjugated, is an adenovirus, a polycation, a cationic lipid or a peptide or targeted vector.

16. A method as claimed in claim 15 wherein said transfer molecule is attached to, associated with, or conjugated to a vector, and said vector is attached to, associated with, or conjugated to, a carrier molecule, targeting molecule or vector.

17. A method as claimed in claim 15 wherein said polycation is poly-L-lysine or poly-D-lysine.

18. A method as claimed in claim 15 wherein said cationic lipid is 1,2-dioleoyl-3-trimethylammonium propane.

19. A method as claimed in claim 1 wherein said carrier molecules are a liposome or lipid based construct, preferably containing at least one cationic lipid.

20. A method as claimed in claim 1 wherein the method is performed in a plurality of cells and at least 50% of said cells into which said transfer molecule is introduced are not killed.

21. A method as claimed in claim 1 wherein the irradiation step is 1 to 10 minutes in length.

22. A method of treating cancer in a patient comprising
    introducing a cytotoxic drug into one or more cells in vitro, in vivo or ex vivo according to a method comprising
        contacting a cancer cell with a photosensitising agent,
        contacting said cancer cell with a cytotoxic drug which comprises a cytotoxic protein, peptide, or fragment thereof, and
        irradiating said cancer cell with light of a wavelength effective to activate the photosensitising agent,
    wherein said cytotoxic drug is taken up into endosomes by the cancer cell and wherein as a consequence of said irradiation said cytotoxic drug is released into the cytosol of said cancer cell, wherein said irradiation is performed prior to cellular uptake of said cytotoxic drug into any intracellular compartment, and where necessary administering said cell to said patient.

23. A method as claimed in claim 22, wherein one or both of the photosensitising agent and the cytotoxic drug is attached to, associated with, or conjugated to, one or more carrier molecules, targeting molecules or vectors.

24. A method as claimed in claim 16 wherein said vector to which, or with which, said transfer molecule is attached, associated or conjugated is an adenovirus.

* * * * *